US010251910B2

(12) United States Patent
Sherman et al.

(10) Patent No.: US 10,251,910 B2
(45) Date of Patent: *Apr. 9, 2019

(54) SODIUM NITRITE-CONTAINING PHARMACEUTICAL COMPOSITIONS

(71) Applicant: Hope Medical Enterprises, Inc., Scottsdale, AZ (US)

(72) Inventors: Craig Sherman, Scottsdale, AZ (US); Anthony James Lepine, Greendale, WI (US); Catherine Marie Smith, Grafton, WI (US); Kevin Robert Wirtz, Belgium, WI (US); Erich Schulze, Mission Viejo, CA (US)

(73) Assignee: Hope Medical Enterprises, Inc., Scottsdale, AZ (US)

(*) Notice: Subject to any disclaimer, the term of this patent is extended or adjusted under 35 U.S.C. 154(b) by 13 days.

This patent is subject to a terminal disclaimer.

(21) Appl. No.: 15/599,617

(22) Filed: May 19, 2017

(65) Prior Publication Data

US 2017/0252368 A1 Sep. 7, 2017

Related U.S. Application Data

(60) Continuation of application No. 15/249,746, filed on Aug. 29, 2016, now Pat. No. 9,687,505, which is a continuation of application No. 14/547,255, filed on Nov. 19, 2014, now Pat. No. 9,597,354, which is a continuation of application No. 14/042,783, filed on Oct. 1, 2013, now Pat. No. 8,920,852, which is a division of application No. 12/703,448, filed on Feb. 10, 2010, now Pat. No. 8,568,793.

(60) Provisional application No. 61/224,021, filed on Jul. 8, 2009, provisional application No. 61/151,820, filed on Feb. 11, 2009.

(51) Int. Cl.
| *A61K 33/00* | (2006.01) |
| *A61K 31/04* | (2006.01) |
| *A61K 9/00* | (2006.01) |
| *A61K 47/02* | (2006.01) |
| *C01B 21/50* | (2006.01) |
| *A61K 31/17* | (2006.01) |
| *A61K 31/4418* | (2006.01) |
| *A61K 31/4709* | (2006.01) |
| *A61K 31/519* | (2006.01) |
| *A61K 9/08* | (2006.01) |

(52) U.S. Cl.
CPC ............ *A61K 33/00* (2013.01); *A61K 9/0019* (2013.01); *A61K 9/08* (2013.01); *A61K 31/17* (2013.01); *A61K 31/4418* (2013.01); *A61K 31/4709* (2013.01); *A61K 31/519* (2013.01); *C01B 21/50* (2013.01); *Y10T 436/204998* (2015.01)

(58) Field of Classification Search
None
See application file for complete search history.

(56) References Cited

U.S. PATENT DOCUMENTS

| 2,032,699 | A | 3/1936 | Hayes et al. |
| 2,933,377 | A | 4/1960 | Doubt et al. |
| 3,965,247 | A | 6/1976 | Hecklinger et al. |
| 4,292,311 | A | 9/1981 | Sarnoff et al. |
| 5,156,850 | A * | 10/1992 | Wong .............. A61K 9/0004 424/472 |
| H1126 | H | 1/1993 | Pan et al. |
| 6,251,354 | B1 | 6/2001 | Greenwell et al. |
| 6,855,306 | B2 | 2/2005 | Bortle et al. |
| 8,496,973 | B2 | 7/2013 | Sherman et al. |
| 8,557,300 | B2 | 10/2013 | Hassett |
| 8,568,793 | B2 | 10/2013 | Sherman et al. |
| 8,715,746 | B2 | 5/2014 | Sherman et al. |
| 8,920,852 | B2 | 12/2014 | Sherman et al. |
| 9,687,506 | B2 * | 6/2017 | Sherman .............. A61K 33/00 |
| 2005/0036949 | A1 | 2/2005 | Tudor et al. |
| 2006/0276339 | A1 | 7/2006 | Windsor et al. |
| 2006/0182815 | A1 | 8/2006 | Gladwin et al. |
| 2007/0154569 | A1 | 7/2007 | Gladwin et al. |
| 2007/0239107 | A1 | 10/2007 | Lundberg et al. |
| 2008/0069779 | A1 | 3/2008 | Tamarkin et al. |
| 2008/0260865 | A1 | 10/2008 | Hassett |
| 2009/0235818 | A1 | 9/2009 | Hensman |
| 2011/0311653 | A1 * | 12/2011 | Kevil .............. A61K 33/00 424/696 |

FOREIGN PATENT DOCUMENTS

| WO | WO 2005/004884 A2 | 1/2005 |
| WO | WO 2005/007173 A1 | 1/2005 |

OTHER PUBLICATIONS

"Natriumnitrit ED—Sigma-Aldrich," Jan. 1, 2007, Handbuch Feinchemjkalien, pp. 1832-1833 (XP009160951).
Aldrich, Handbook of Fine Chemicals, Sigma-Aldrich Co., 2007-2008, entry for Sodium Nitrite.
Beznosikov, 1965, "Peculiarities in the growth of sodium nitrite crystals," Sovie Physics-Crystallography, vol. 10(2):214-215.
E-mail from Gregory Stachowiak, Scientist, Technical Service Associate, Sigma-Aldrich, relating to sodium nitrite purity (Jun. 13-15, 2011).
Federal Register 77(229) 71006-71008, Nov. 28, 2012.
GE—Water & Process Technologies Analytical Instruments—Sievers InnovOx—Laboratory TOC Analyzer—Fact Sheet (2008).
General Chemical—Sodium Nitrite, Free-Flowing Food Grade—Product Data Sheet, www.generalChemical.com (2008).

(Continued)

*Primary Examiner* — Robert T. Crow
*Assistant Examiner* — John P Nguyen
(74) *Attorney, Agent, or Firm* — Jones Day

(57) ABSTRACT

Provided herein are pharmaceutically acceptable sodium nitrite and pharmaceutical compositions thereof. Also provided herein are methods for determining the total non-volatile organic carbon in a sodium nitrite-containing sample. Further provided herein are methods for producing pharmaceutically acceptable sodium nitrite. Still further provided herein are methods of treatment comprising the administration of pharmaceutically acceptable sodium nitrite.

10 Claims, No Drawings

(56) References Cited

OTHER PUBLICATIONS

Official Monographs / "Sodium Nitrite," USP XXII, 1263-1264 (1990).
Sodium Nitrite grades, BASF, 2002, pp. 1-8.
Supplementary European Search Report, Application No. EP 10741692.7, dated Jul. 11, 2012.
USP31-NF26, United States Pharmacopeial, 2008, pp. 3524.
Yadav et al., 1987, "Purification and growth of ferroelectric sodium nitrite single crystals using zone-refining technique," Cryst. Res. Tech., 22(9)k151-K153.
Basireddy, et al., 2006, Effects of sodium nitrite on ischemia-reperfusion injury in the rat kidney, American Journal of Physiology—Renal Physiology, 2006, F779-F786, 290.4.
Krstic, Illustrated Encyclopedia of Human Histology, p. 101, 1984.

* cited by examiner

SODIUM NITRITE-CONTAINING PHARMACEUTICAL COMPOSITIONS

This application is a continuation of U.S. patent application Ser. No. 15/249,746, filed Aug. 29, 2016, currently allowed, which is a continuation of U.S. patent application Ser. No. 14/547,255, filed Nov. 19, 2014, now U.S. Pat. No. 9,597,354, issued Mar. 21, 2017, which is a continuation of U.S. patent application Ser. No. 14/042,783, filed Oct. 1, 2013, now U.S. Pat. No. 8,920,852, issued Dec. 30, 2014, which is a divisional of U.S. patent application Ser. No. 12/703,448, filed Feb. 10, 2010, now U.S. Pat. No. 8,568,793, issued Oct. 29 2013, which claims the benefit of U.S. Provisional Application No. 61/151,820, filed Feb. 11, 2009 and U.S. Provisional Application No. 61/224,021, filed Jul. 8, 2009, each of which is incorporated by reference herein in its entirety.

FIELD

Provided herein are pharmaceutically acceptable sodium nitrite and pharmaceutical compositions thereof. Also provided herein are methods for determining the total non-volatile organic carbon in a sodium nitrite-containing sample. Further provided herein are methods for producing pharmaceutically acceptable sodium nitrite. Still further provided herein are methods of treatment comprising the administration of pharmaceutically acceptable sodium nitrite.

BACKGROUND

Sodium nitrite has numerous applications, such as uses as a food additive and a pharmaceutical ingredient. Even though thousands of metric tons of sodium nitrite are produced annually, only a few kilograms are utilized pharmaceutically for the production of sodium nitrite injection as currently indicated as a treatment for cyanide poisoning. It has been reported that sodium nitrite is an effective treatment for hydrogen sulfide poisoning (Hall and Rumack, *Vet Human Toxicol.* 1997, 39, 152-154). It has been recently reported that sodium nitrite is an effective vasodilator, which may be used to treat many conditions, including heart attack, stroke, sickle cell anemia, respiratory diseases, and bacterial, viral or fungal infections (WO 2005/004884, WO 2005/007173, U.S. Patent Application Publication Nos. 2004/0105898, 2005/0036949, and 2008/0260865, the disclosure of each of which is incorporated herein by reference in its entirety). It has also been recently reported that sodium nitrite augments angiogenesis and arteriogenesis, which may be used to treat ischemic conditions including angina and claudication. (Kumar et al, *Proc. Natl. Acad. Sci. USA* 2008, 105, 7540-7545). Sodium nitrite is also useful in connection with reducing the risk of hospital-acquired infections, such as nocosomial infections, originating from the insertion of medical devices, such as catheters (U.S. Patent Application Publication No. 2007/0239107, the disclosure which is incorporated herein by reference in its entirety).

The manufacture of pharmaceutical products in the United States is regulated by the Food and Drug Administration (FDA). Since the passage of the Federal Food Drug and Cosmetic Act in 1938, the FDA has required new pharmaceutical products and their corresponding active ingredients to be manufactured in accordance with the exacting requirements of "pharmaceutical grade" Good Manufacturing Practices as detailed in the United States Code of Federal Regulations 21 CFR 211. Because of the relatively small quantity of sodium nitrite that is currently used to formulate pharmaceutical products, no raw material supplier presently manufactures sodium nitrite in accordance with "pharmaceutical grade" Good Manufacturing Practices.

In addition to regulating manufacturing practices, the FDA establishes stringent quality specifications for each new pharmaceutical product and its corresponding active ingredients. A pharmaceutical product is classified as "new" if it was introduced to the market after the passage of the Food Drug and Cosmetic Act in 1938. As mandated in this Act, the FDA requires a new pharmaceutical product and its active ingredients to be manufactured in accordance with "pharmaceutical grade" Good Manufacturing Practices and to meet applicable quality specifications. When the Food Drug and Cosmetic Act was enacted in 1938, pharmaceuticals that were already on the market were classified as "grandfathered drugs" and were permitted to remain on the market without formal FDA approval if the product and its labeling remain unchanged. Any change to the product or its labeling would cause the "grandfathered drug" to become a "new" drug that is subject to FDA-imposed regulations and quality standards. Currently available sodium nitrite injection that is labeled solely for use as a treatment of cyanide poisoning is a "grandfathered medication". Consequently, the product formulation and corresponding quality specifications have remain unchanged for decades.

In anticipation of the receipt of a New Drug Application for a sodium nitrite pharmaceutical product, the FDA recently announced that sodium nitrite raw material for a new pharmaceutical product must be manufactured in accordance with "pharmaceutical grade" Good Manufacturing Practices and it must conform to a new set of quality specifications. This new set of quality specifications is more expansive and stringent than the existing quality specifications. Currently available sodium nitrite raw material does not meet the new set of FDA quality standards and is unsuitable for use in the formulation of a new pharmaceutical product. Consequently, there is a clear and unmet need for purified sodium nitrite raw material that is manufactured in accordance with "pharmaceutical grade" Good Manufacturing Practices and that meets the new set of quality specifications in order to translate recent nitrite-related research discoveries into FDA-approved clinical therapies.

Another hurdle in developing pharmaceutical grade sodium nitrite is the lack of an effective analytical method to determine total non-volatile organic carbon in a sodium nitrite-containing sample, which is one of the new FDA-imposed quality standards. The conventional method for total non-volatile organic carbon determination requires that any inorganic carbon must be removed before measuring the organic carbon content in a sample. This is typically achieved by adding acid. At low pH, the inorganic carbon is converted to carbon dioxide, which is then purged from the sample. The sample is then routed to a combustion chamber with a catalyst and a temperature of approximately 680° C. to convert organic carbon to carbon dioxide. The quantity of carbon dioxide thus produced is then determined using an infrared detector. However, this conventional method cannot be used to analyze a sodium nitrite-containing sample. Sodium nitrite explodes when exposed to temperatures in excess of 538° C. Also, sodium nitrite is converted into nitric oxide when exposed to an acid, and the nitric oxide thus formed may pass into the detector along with carbon dioxide, interfere with the detection, and produce false signals. Furthermore, sodium nitrite may precipitate during the analysis. Deposits of sodium nitrite salt on the catalyst can foul the catalyst and preclude complete combustion. Deposits of sodium nitrite salt on the optics can also decrease the light intensity of the radiation source. Therefore, there is also a need for an analytical method for determining total non-volatile organic carbon in a sodium nitrite-containing sample.

Another hurdle in developing pharmaceutical grade sodium nitrite is the presence of anti-caking material in non-pharmaceutical grade sodium nitrite. Sodium nitrite is hygroscopic. To prevent the absorption of water over time and to facilitate industrial usage, manufacturers of non-pharmaceutical grade sodium nitrite generally add anti-caking material with surfactant characteristics, such as sodium alkyl naphthalene sulfonate. Even if a manufacturer of non-pharmaceutical grade sodium nitrite that contains an anti-caking agent produces a batch of sodium nitrite without the addition of an anti-caking agent, trace quantities of the anti-caking agent that exceed the new FDA-imposed quality standards may be present. Therefore, any anti-caking material in sodium nitrite must be detected, quantified, and limited in order to produce pharmaceutical grade sodium nitrite.

SUMMARY OF THE DISCLOSURE

Provided herein is sodium nitrite which contains no greater than about 0.02% by weight of sodium carbonate and/or no greater than about 10 ppm (0.001% by weight) of an anti-caking agent.

Also provided herein are pharmaceutical compositions, which comprise sodium nitrite and a pharmaceutically acceptable excipient, wherein the sodium nitrite contains no greater than about 0.02% by weight of sodium carbonate or no greater than about 10 ppm (0.001% by weight) of an anti-caking agent.

Also provided herein are methods of determining the total non-volatile organic carbon in a sodium nitrite-containing sample, which comprises the steps of: a) adding an inorganic acid in a predetermined amount to an aqueous sample solution that contains sodium nitrite; b) adding an oxidizer in a predetermined amount to the sample solution; and c) converting the organic carbon in the sample solution into carbon dioxide under a supercritical water oxidation condition; wherein the final amount of the inorganic acid is no less than 2% of the final volume of the sample solution or the final amount of the oxidizer is no less than 20% of the final volume of the sample solution.

Also provided herein are methods for preparing the pharmaceutically acceptable sodium nitrite, which comprises the steps of: a) contacting non-pharmaceutical grade sodium nitrite (wherein non-pharmaceutical grade sodium nitrite includes, but is not limited to, food grade sodium nitrite) with a first solvent at a first temperature; b) heating the mixture to a second temperature; c) cooling the mixture to a third temperature; d) contacting the mixture with activated carbon; e) cooling the mixture to a fourth temperature; and f) contacting the mixture with a second solvent.

Also provided herein are methods for treating an acute poisoning, including, but not limited to, cyanide poisoning and hydrogen sulfide poisoning, which comprises administering to a subject a therapeutically effective amount of sodium nitrite provided herein.

Also provided herein are methods for treating a cardiovascular disease or a condition associated with the cardiovascular system, including, but not limited to, high blood pressure, pulmonary hypertension, angina, claudication, cerebral vasospasm, and tissue ischemia-reperfusion injury, which comprises administering to a subject a therapeutically effective amount of sodium nitrite provided herein.

Also provided herein are methods for treating a respiratory disease or a condition associated with the tracheopulmonary system, including, but not limited to, cystic fibrosis, pulmonary tuberculosis, mycotic pneumonia, bacterial pneumonia, viral pneumonia, pulmonary abscess, pulmonary hypertension, pulmonary embolism, and pulmonary vasospasm, which comprises administering to a subject a therapeutically effective amount of sodium nitrite provided herein.

Also provided herein are methods for treating a dermatological disease or a condition associated with the skin, including, but not limited to, bacterial infection of the skin, mycotic infection of the skin, viral infection of the skin, mycotic infection of the nails, bacterial infection of the nails, viral infection of the nails, mycotic infection of the nailbeds, bacterial infection of the nailbeds, viral infection of the nailbeds, psoriasis, scleroderma, inflammation of the skin, inflammation of the nails, and inflammation of the nailbeds, which comprises administering to a subject a therapeutically effective amount of sodium nitrite provided herein.

Also provided herein are methods for treating, preventing or reducing the risk of hospital-acquired infections, such as nocosomial infections, which can originate from the insertion of a device (e.g., a medical device) and/or the use of a device in the body.

DETAILED DESCRIPTION

To facilitate understanding of the disclosure set forth herein, a number of terms are defined below.

Generally, the nomenclature used herein and the laboratory procedures in inorganic chemistry, analytical chemistry, organic chemistry, medicinal chemistry, and pharmacology described herein are those well known and commonly employed in the art. Unless defined otherwise, all technical and scientific terms used herein generally have the same meaning as commonly understood by one of ordinary skill in the art to which this disclosure belongs. In the event that there is a plurality of definitions for a term used herein, those in this section prevail unless stated otherwise.

The term "subject" refers to an animal, including, but not limited to, a primate (e.g., human), cow, sheep, goat, horse, dog, cat, rabbit, rat, or mouse. The terms "subject" and "patient" are used interchangeably herein in reference, for example, to a mammalian subject, such as a human subject. In one embodiment, the subject has or is at risk for a disease, disorder or condition provided herein. In another embodiment, the patient has or is at risk for a disease, disorder or condition wherein the disease, disorder or condition, or a symptom thereof, can be treated, prevented or ameliorated by the administration of sodium nitrite.

The term "host" refers to a unicellular or multicellular organism in which a virus can replicate, including, but not limited to, a cell, cell line, and animal, such as human.

The terms "treat," "treating," and "treatment" are meant to include alleviating or abrogating a disorder, disease, or condition, or one or more of the symptoms associated with the disorder, disease, or condition; or alleviating or eradicating the cause(s) of the disorder, disease, or condition itself.

The terms "prevent," "preventing," and "prevention" are meant to include a method of delaying and/or precluding the onset of a disorder, disease, or condition, and/or its attendant symptom(s); barring a subject from acquiring a disease; or reducing a subject's risk of acquiring a disorder, disease, or condition.

The term "therapeutically effective amount" is meant to include the amount of a compound that, when administered, is sufficient to prevent development of, or alleviate to some extent, one or more of the symptoms of the disorder, disease, or condition being treated. The term "therapeutically effective amount" also refers to the amount of a compound that is sufficient to elicit the biological or medical response of a cell, tissue, system, animal, or human, which is being sought by a researcher, veterinarian, medical doctor, or clinician.

The term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, excipient, solvent, or encapsulating material. In one embodiment, each component is "pharmaceutically acceptable" in the sense of being compatible with the other ingredients of a pharmaceutical formulation, and suitable for use in contact with cells, tissues, or organs of humans and animals without excessive toxicity, irritation, allergic response, immunogenicity, or other problems or complications, commensurate with a reasonable benefit/risk ratio. See, *Remington: The Science and Practice of Pharmacy*, 21st Edition, Lippincott Williams & Wilkins: Philadelphia, Pa., 2005; *Handbook of Pharmaceutical Excipients*, 5th Edition, Rowe et al., Eds., The Pharmaceutical Press and the American Pharmaceutical Association: 2005; and *Handbook of Pharmaceutical Additives*, 3rd Edition, Ash and Ash Eds., Gower Publishing Company: 2007; *Pharmaceutical Preformulation and Formulation*, Gibson Ed., CRC Press LLC: Boca Raton, Fla., 2004.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 15%, 10%, 9%, 8%, 7%, 6%, 5%, 4%, 3%, 2%, 1%, 0.5%, or 0.05% of a given value or range. In certain embodiments, it is contemplated that the values preceded by the term "about" or "approximately" are exact.

The terms "active ingredient" and "active substance" refer to a compound, which is administered, alone or in combination with one or more pharmaceutically acceptable excipients, to a subject for treating, preventing, or ameliorating one or more symptoms of a condition, disorder, or disease. As used herein, "active ingredient" and "active substance" may be an optically active isomer of a compound described herein.

The terms "drug," "therapeutic agent," and "chemotherapeutic agent" refer to a compound, or a pharmaceutical composition thereof, which is administered to a subject for treating, preventing, or ameliorating one or more symptoms of a condition, disorder, or disease.

The term "anti-solvent" refers to a liquid that is added to a solvent to reduce the solubility of a compound in that solvent, resulting in precipitation or crystallization of the compound.

The term "sodium phosphate" refers to sodium dihydrogen phosphate ($NaH_2PO_4$), disodium hydrogen phosphate ($Na_2HPO_4$), or trisodium phosphate ($Na_3PO_4$). In certain embodiments, the sodium phosphate is sodium dihydrogen phosphate. In certain embodiments, the sodium phosphate is disodium hydrogen phosphate. In certain embodiments, the sodium phosphate is trisodium phosphate.

Sodium Nitrite

Provided herein are purified forms of sodium nitrite ($NaNO_2$), also known as monosodium salt of nitrous acid. In one embodiment, provided herein is pharmaceutically acceptable sodium nitrite. In another embodiment, provided herein are forms of sodium nitrite meeting one, more than one, or all FDA standards for sodium nitrite for pharmaceutical use.

In one embodiment, the pharmaceutically acceptable sodium nitrite is white to off-white solid.

In one embodiment, the pharmaceutically acceptable sodium nitrite has a positive identification test for sodium determined according to method <191> in USP XXXII (2009).

In one embodiment, the pharmaceutically acceptable sodium nitrite has a positive identification test for nitrite determined according to method <191> in USP XXXII (2009).

In one embodiment, the sodium nitrite provided herein contains no less than about 97% by weight and/or no greater than about 101% by weight of sodium nitrite. In certain embodiments, the amount of sodium nitrite in the sodium nitrite provided herein is determined according to USP colormetric assay (USP XXXII (2009)). In certain embodiments, the amount of sodium nitrite in the sodium nitrite provided herein is determined by an ion chromatography. In certain embodiments, the amount of sodium nitrite in the sodium nitrite provided herein is determined by an ion chromatography is coupled with suppressed conductivity detection as described herein.

In another embodiment, the sodium nitrite provided herein has a pH between about 8 to about 9 when measured in a 10% solution at 25° C. In certain embodiments, the pH of the sodium sodium provided herein is measured using a pH meter. In certain embodiments, the pH of the sodium sodium provided herein is determined according to Method 791 in USP XXXII (2009).

In yet another embodiment, the sodium nitrite provided herein has a loss on drying of no greater than about 0.25% by weight. In certain embodiments, the loss on drying of the sodium nitrite provided herein is quantitated according to Method 731 in USP XXXII (2009).

In yet another embodiment, the sodium nitrite provided herein has water content of no greater than about 0.5% by weight. In certain embodiments, the water content in the sodium nitrite provided herein is determined by Karl Fischer method. In certain embodiments, the water content in the sodium nitrite provided herein is quantitated according to Method 921 in USP XXXII (2009).

In yet another embodiment, the heavy metal content in the sodium nitrite provided herein is no greater than about 10 ppm of a heavy metal. The heavy metal content in the sodium nitrite provided herein is determined according to Method 231 in USP XXXII (2009).

In yet another embodiment, the sodium nitrite provided herein contains no greater than about 0.4% by weight of sodium nitrate. In certain embodiments, the amount of sodium nitrate in the sodium nitrite provided herein is determined by an ion chromatography method in coupled with suppressed conductivity detection as described herein.

In yet another embodiment, the sodium nitrite provided herein contains no greater than about 0.02% by weight of sodium carbonate. In certain embodiments, the amount of sodium carbonate in the sodium nitrite provided herein is determined by mixing the sample with an acid to convert carbonate to carbon dioxide and venting the carbon dioxide to a non-dispersive infrared detector for measurement.

In yet another embodiment, the sodium nitrite provided herein contains no greater than about 0.005% by weight of insoluble matter. In certain embodiments, the amount of insoluble material in the sodium nitrite provided herein is determined by dissolving 10 grams of the sodium nitrite provided herein in 100 mL of water, the solution is heated to boiling for 1 hour, the solution is filtered, washed with hot water, dried, cooled in a desiccator, and weighed.

In yet another embodiment, the sodium nitrite provided herein contains no greater than about 0.005% by weight of chloride. In certain embodiments, the chloride content in the sodium nitrite provided herein is determined according to Method 221 in USP XXXII (2009).

In yet another embodiment, the sodium nitrite provided herein contains no greater than about 0.01% by weight of sulfate. In certain embodiments, the sulfate content in the sodium nitrite provided herein is determined according to Method 221 in USP XXXII (2009).

In yet another embodiment, the sodium nitrite provided herein contains no greater than about 0.001% by weight of iron. In certain embodiments, the iron content in the sodium nitrite provided herein is determined using inductively coupled plasma mass spectrometry (ICP-MS). In certain embodiments, the iron content in the sodium nitrite provided herein is determined using inductively coupled plasma-optical emission spectroscopy (ICP-OES). In certain embodiments, the iron content in the sodium nitrite provided herein is determined according to Method 241 in USP XXXII (2009).

In yet another embodiment, the sodium nitrite provided herein contains no greater than about 0.01% by weight of calcium. In certain embodiments, the calcium content in the sodium nitrite provided herein is determined using ICP-MS. In certain embodiments, the calcium content in the sodium nitrite provided herein is determined using flame emission spectrometry (FES).

In yet another embodiment, the sodium nitrite provided herein contains no greater than about 0.005% by weight of potassium. In certain embodiments, the potassium content in the sodium nitrite provided herein is determined using ICP-MS. In certain embodiments, the potassium content in the sodium nitrite provided herein is determined using FES.

In yet another embodiment, the sodium nitrite provided herein contains no greater than about 10 ppm, no greater than about 100 ppm, no greater than about 500 ppm, no greater than about 1000 ppm, or no greater than 5000 ppm of ethanol. In certain embodiments, the content of organic volatile impurities is determined according to Method 467 in USP XXXII (2009).

In yet another embodiment, the sodium nitrite provided herein contains no greater than about 10 ppm, no greater than about 100 ppm, no greater than about 500 ppm, no greater than about 1000 ppm, or no greater than 3000 ppm of methanol. In certain embodiments, the content of organic volatile impurities is determined according to Method 467 in USP XXXII (2009).

In yet another embodiment, the sodium nitrite provided herein contains total non-volatile organic carbon of no greater than about 2.5 ppm, no greater than about 6 ppm, no greater than about 8 ppm, no greater than about 10 ppm, no greater than about 20 ppm, no greater than about 25 ppm, or no greater than about 50 ppm. In certain embodiments, the sodium nitrite provided herein contains total non-volatile organic carbon (NVOC) or equivalent non-purgable organic carbon (NPOC) of no greater than about 10 ppm. In certain embodiments, the sodium nitrite provided herein contains total non-volatile organic carbon of no greater than about 7.9 ppm. In certain embodiments, the sodium nitrite provided herein contains total non-volatile organic carbon of no greater than about 5.6 ppm. In certain embodiments, the total non-volatile organic carbon in the sodium nitrite provided herein is determined using methods described herein.

In yet another embodiment, the sodium nitrite provided herein contains no greater than about 0.05 ppm of mercury. In certain embodiments, the mercury content in the sodium nitrite provided herein is determined using ICP-MS. In certain embodiments, the mercury content in the sodium nitrite provided herein is determined using ICP-OES. In certain embodiments, the mercury content in the sodium nitrite provided herein is determined according to Method 261 in USP XXXII (2009).

In yet another embodiment, the sodium nitrite provided herein contains no greater than about 2 ppm of aluminum. In yet another embodiment, the sodium nitrite provided herein contains no greater than about 0.2 ppm of aluminum. In certain embodiments, the aluminum content in the sodium nitrite provided herein is determined using ICP-MS. In certain embodiments, the aluminum content in the sodium nitrite provided herein is determined using ICP-OES. In certain embodiments, the aluminum content in the sodium nitrite provided herein is determined according to Method 206 in USP XXXII (2009).

In yet another embodiment, the sodium nitrite provided herein contains no greater than about 3 ppm of arsenic. In yet another embodiment, the sodium nitrite provided herein contains no greater than about 1 ppm of arsenic. In certain embodiments, the arsenic content in the sodium nitrite provided herein is determined using ICP-MS. In certain embodiments, the arsenic content in the sodium nitrite provided herein is determined using ICP-OES. In certain embodiments, the arsenic content in the sodium nitrite provided herein is determined according to Method 211 in USP XXXII (2009).

In yet another embodiment, the sodium nitrite provided herein contains no greater than about 10 ppm (0.001% by weight) of an anti-caking agent. In certain embodiments, the anti-caking agent is sodium alkyl-naphthalene sulfonate. In certain embodiments, the amount of sodium alkyl-naphthalene sulfonate in the sodium nitrite provided herein is quantitated using mass spectrometry and liquid chromatography method as described herein.

In yet another embodiment, the sodium nitrite provided herein contains no greater than about 0.003% by weight of selenium. In certain embodiments, the selenium content in the sodium nitrite provided herein is determined using ICP-MS. In certain embodiments, the selenium content in the sodium nitrite provided herein is determined using ICP-OES. In certain embodiments, the selenium content in the sodium nitrite provided herein is determined according to Method 291 in USP XXXII (2009).

In yet another embodiment, the total aerobic count of microbial load in the sodium nitrite provided herein is no greater than about 100 CFU/g. The total aerobic count of microbial load in the sodium nitrite provided herein is quantitated according to Method 61 in USP XXXII (2009).

In yet another embodiment, the total yeast and mold count in the sodium nitrite provided herein is no greater than about 20 CFU/g. The total yeast and mold count in the sodium nitrite provided herein is quantitated according to Method 61 in USP XXXII (2009).

In yet another embodiment, the sodium nitrite provided herein contains no greater than about 0.25 EU/mg of bacterial endotoxins. The amount of bacterial endotoxins in the sodium nitrite provided herein is quantitated according to Method 85 in USP XXXII (2009).

In yet another embodiment, the sodium nitrite provided herein contains less than about 0.1 ppm of sodium phosphate. In certain embodiments, the sodium nitrite provided herein contains does not contain a detectable amount of sodium phosphate. In certain embodiments, the sodium phosphate is disodium hydrogen phosphate. In certain embodiments, the sodium phosphate is trisodium phosphate.

In yet another embodiment, the sodium nitrite provided herein is characterized by one or more of the following:

containing no less than about 97% by weight and/or no greater than about 101% by weight of sodium nitrite;

having a positive identification test for sodium;

having a positive identification test for thiosulfate;

having a pH between about 8 to about 9 when measured in a 10% solution at 25° C.;

having a loss on drying of no greater than about 0.25% or about 0.01% by weight;

having water content of no greater than about 0.5% by weight;

having heavy metal content of no greater than about 10 ppm;

containing no greater than about 0.4% by weight of sodium nitrate;

containing no greater than about 0.02%, about 0.01% or about 0.001% by weight of sodium carbonate;

containing no greater than about 0.005% or about 0.001% by weight of insoluble matter;

containing no greater than about 0.005% by weight of chloride;

containing no greater than about 0.01% by weight of sulfate;

containing no greater than about 0.001% by weight of iron;

containing no greater than about 0.01% by weight of calcium;

containing no greater than about 0.005% or about 0.001% by weight of potassium;

containing no greater than about 0.1% by weight ethanol or no greater than about 10 ppm, no greater than about 100 ppm, no greater than about 500 ppm, no greater than about 1000 ppm, or no greater than 5000 ppm of ethanol;

containing no greater than about 10 ppm, no greater than about 100 ppm, no greater than about 500 ppm, no greater than about 1000 ppm, or no greater than 3000 ppm of methanol;

having total non-volatile organic carbon or equvalent of no greater than about 2.5 ppm, no greater than about 5.6 ppm, no greater than about 6 ppm, no greater than about 7.9 ppm, no greater than about 8 ppm, no greater than about 10 ppm, no greater than about 20 ppm, no greater than about 25 ppm, or no greater than about 50 ppm; and in one embodiment, no greater than about 10 ppm;

containing no greater than about 0.05 ppm of mercury;

containing no greater than about 2 ppm or 0.2 ppm of aluminum;

containing no greater than about 3 ppm or about 1 ppm of arsenic;

containing no greater than about 10 ppm or about 0.001% by weight of an anti-caking agent;

containing no greater than about 0.003% or about 0.001% by weight of selenium (ICP-OES or equivalent);

having a total aerobic count of microbial load of no greater than about 100 CFU/g;

having a total yeast and mold count of no greater than about 20 CFU/g;

containing no greater than about 0.25 EU/mg or about 0.018 EU/mg of bacterial endotoxins; and containing no greater than about 0.1 ppm of sodium phosphate.

In one embodiment, provided herein is sodium nitrite having one or more of the characteristics referenced herein produced by a process provided herein. In one embodiment, provided herein is sodium nitrite having one or more of the characteristics set forth in Table 1.

Preparation of Sodium Nitrite

Also provided herein are methods for preparing the pharmaceutically acceptable sodium nitrite, which comprises the steps of: a) contacting non-pharmaceutical grade sodium nitrite (wherein non-pharmaceutical grade sodium nitrite includes, but is not limited to, food grade sodium nitrite) with a first solvent at a first temperature; b) heating the mixture to a second temperature; c) cooling the mixture to a third temperature; d) contacting the mixture with activated carbon; e) cooling the mixture to a fourth temperature; and f) contacting the mixture with a second solvent. In certain embodiments, the method further comprises an isolation step after one or more of the steps provided herein in which the sodium nitrite is isolated under inert atmosphere (e.g., $N_2$ or Ar) by a conventional method, such as filtration or centrifugation, followed by drying (e.g., vacuum oven drying, air drying, or desicator drying). In one embodiment, the first solvent is a polar solvent, such as water (including but not limited to water, purified water, utrapure water, and water for injection). In another embodiment, the second solvent is an organic solvent, such as ethyl alcohol.

In certain embodiments, the sodium nitrite is dried under inert atmosphere at an elevated temperature of no greater than the melting point of sodium nitrite. In certain embodiments, the elevated temperature is about 60-70° C. or ≤65° C. In particular embodiments, the elevated temperature is about 60° C. or about 65° C.

Suitable solvents for use in the method provided herein include, but are not limited to, water (including but not limited to water, purified water, utrapure water, and water for injection), methanol, ethanol, isopropanol (IPA), 1-propanol, 2-methoxyethanol, 2-ethoxyethanol, ethyleneglycol, ethyl alcohol, acetone, N,N-dimethylformamide (DMF), N,N-dimethylacetamide, acetonitrile (ACN), dimethyl sulfoxide (DMSO), N-methyl pyrrolindone, tetrahydrofuran (THF), dioxane, acetic acid, trichloroacetic acid, trifluoroacetic acid, and a mixture thereof. In one embodiment, the solvent is aqueous. In another embodiment, the solvent is water. In yet another embodiment, the solvent is a mixture of water with a water-miscible solvent, including, but not limited to, methanol, ethanol, isopropanol (IPA), 1-propanol, 2-methoxyethanol, 2-ethoxyethanol, ethyleneglycol, acetone, N,N-dimethylformamide (DMF), N,N-dimethylacetamide, acetonitrile (ACN), dimethyl sulfoxide (DMSO), N-methyl pyrrolindone, tetrahydrofuran (THF), dioxane, acetic acid, trichloroacetic acid, trifluoroacetic acid, and a mixture thereof.

In certain embodiments, the sodium nitrite is prepared from a solution or slurry of sodium nitrite in a solvent using conventional methods, including, but not limited to, cooling, chilling, solvent evaporation, or addition of an anti-solvent.

In one embodiment, the method for preparing the sodium nitrite provided herein comprises the steps of: (a) preparing a solution of sodium nitrite in a solvent at a first temperature under inert atmosphere; and (b) generating sodium nitrite at a second temperature under inert atmosphere. To accelerate the formation of the sodium nitrite, the method may also comprise a seeding step by seeding the solution with crystals of sodium nitrite under inert atmosphere, prior to or during step (b). In certain embodiments, the method further comprises an isolation and drying step as described herein.

In certain embodiments, the solution of step (a) is prepared as a saturated or nearly saturated solution at the first temperature. The saturated or nearly saturated solution is prepared by dissolving a sufficient amount of sodium nitrite in the solvent at a temperature that is higher than the first temperature, such that, when the solution is allowed to cool to the first temperature, a saturated or nearly saturated solution is obtained. The sufficient amount of sodium nitrite can be estimated based on the solubility of sodium nitrite in the solvent at the first temperature, which is known in the art or can be determined using a method known to a person skilled in the art.

In certain embodiments, the first temperature ranges from room temperature to about the boiling point of the solvent employed and no greater than the melting point of sodium nitrite (about 270° C.). In certain embodiments, the first temperature ranges from −100 to 100° C., from about −50 to about 50° C., from about −10 to about 30° C., from about 0 to about 30° C., from about 15 to about 30° C. or from about 20 to about 30° C. In certain embodiments, the second temperature ranges from about 10 to about 110° C., from about 20 to about 100° C., from about 20 to about 80° C., from about 20 to about 60° C., from about 20 to about 40° C., from about 30 to about 60° C., from about 45 to about 55° C., from about 20 to about 30° C. or from about 45 to about 55° C. In certain embodiments, the third temperature ranges from −100 to 100° C., from about −50 to about 50° C., from about −10 to about 30° C., from about 0 to about 30° C., from about 15 to about 30° C. or from about 20 to about 30° C. In certain embodiments, the fourth temperature ranges from −100 to 100° C., from about −50 to about 50° C., from about −10 to about 30° C., from about 0 to about 20° C., or from about 0 to about 10° C. To maximize the yield and the efficiency of the method provided herein, the third temperature is normally set to be lower than the second temperature. In certain embodiments, the first temperature is about 24 to about 30° C. and the second temperature is about 45 to about 55° C. In certain embodiments, the first temperature is about 20 to about 30° C., the second temperature is about 45 to about 55° C. and the third temperature is about 20 to about 30° C. In certain embodiments, the first temperature is about 20 to about 30° C., the second temperature is about 45 to about 55° C., the third temperature is about 20 to about 30° C. and the fourth temperature is about 0 to about 10° C. In certain embodiments, the first temperature is about 25° C., the second temperature is about 50° C., the third temperature is about 25° C. and the fourth temperature is about 5° C.

In one embodiment, the sodium nitrite provided herein is obtained by evaporating the solvent from the solution at the second temperature. The solvent evaporation can be facilitated by applying heat and/or vacuum to the solution.

In another embodiment, the sodium nitrite is obtained by cooling the solution to the fourth temperature.

In yet another embodiment, the sodium nitrite is formed by adding an anti-solvent to the solution at a fourth temperature. Suitable anti-solvents include, but are not limited to, methanol, ethanol, isopropanol (IPA), 1-propanol, 2-methoxyethanol, 2-ethoxyethanol, ethyleneglycol, acetone, N,N-dimethylformamide (DMF), N,N-dimethylacetamide, acetonitrile (ACN), dimethyl sulfoxide (DMSO), N-methyl pyrrolindone, tetrahydrofuran (THF), dioxane, acetic acid, trichloroacetic acid, trifluoroacetic acid, and a mixture thereof.

When two solvents are used as a solvent/anti-solvent pair, sodium nitrite has a higher solubility in the solvent than in the anti-solvent. Optionally, the solvent and the anti-solvent in a solvent/anti-solvent pair are at least partially miscible. In certain embodiments, the solvent is water. In certain embodiments, the anti-solvent is a water-miscible solvent. In certain embodiments, the anti-solvent is ethanol.

In yet another embodiment, the sodium nitrite is formed by adding the solution to an anti-solvent at the fourth temperature. In one embodiment, the solvent is water, and the anti-solvent is ethanol.

In certain embodiments, the solution (a) is stirred at room temperature under an inert atmosphere for up to 15, 30, 45 or 60 minutes or longer.

In certain embodiments, one or more of the steps provided herein are carried out under inert atmopshere (e.g., $N_2$ or Ar).

In certain embodiments, a purification step or a filtering step is performed between one or more steps provided herein.

In certain embodiments, filtering steps are carrier out using a glass-microfiber filter (e.g., ≤1.6 μm). In other embodiments, filtering steps are carrier out using an Aurora filter, a Cogeim filter or an Estrella filter.

Other methods known in the art may also be applicable for preparing the pharmaceutically acceptable sodium nitrite provided herein, including spray drying, roller drying, lyophilization, and melt crystallization.

Methods of Characterization

1. Determining the Total Non-Volatile Organic Carbon in Sodium Nitrite

Provided herein are methods of determining the total non-volatile organic carbon in a sodium nitrite-containing sample, which comprise the steps of: (a) adding an inorganic acid in a predetermined amount to an aqueous sample solution that contains sodium nitrite; (b) adding an oxidizer in a predetermined amount to the sample solution; and (c) converting the organic carbon in the sample solution into carbon dioxide under a supercritical water oxidation condition; wherein the final amount of the inorganic acid is no less than about 2% of the final volume of the sample solution or the final amount of the oxidizer is no less than about 20% of the final volume of the sample solution.

In one embodiment, the inorganic acid is phosphoric acid. In another embodiment, the inorganic acid is 6 N phosphoric acid. In yet another embodiment, the final amount of the inorganic acid is no less than about 2% and no greater than about 50% of the final volume of the sample solution. In yet another embodiment, the final amount of the inorganic acid is about 2%, about 3%, about 4%, about 5%, about 6%, about 7%, about 8%, about 9%, about 10%, about 15%, about 20%, about 30%, about 40%, or about 50% of the final volume of the sample solution. In yet another embodiment, the final amount of the inorganic acid is about 6% of the final volume of the sample solution. In still another embodiment, the inorganic acid is 6 N phosphoric acid and the final amount of the inorganic acid is about 6% of the final volume of the sample solution.

In one embodiment, the oxidizer is sodium persulfate. In another embodiment, the oxidizer is 30% sodium persulfate solution. In yet another embodiment, the final amount of the oxidizer is no less than about 20% but no greater than about 90% of the final volume of the sample solution. In yet another embodiment, the final amount of the oxidizer is about 20%, about 25%, about 30%, about 35%, about 40%, about 45%, about 50%, about 55%, about 60%, about 65%, about 70%, about 75%, about 80%, or about 90% of the final volume of the sample solution. In yet another embodiment, the final amount of the oxidizer is about 45% of the final volume of the sample solution. In still another embodiment, the oxidizer is 30% sodium persulfate solution and the final amount of oxidizer is about 45% of the final volume of the sample solution.

In certain embodiments, the organic carbon in the sodium nitrite-containing sample is oxidized according any SCWO processes known in the art, such as those disclosed in U.S. Pat. Nos. 2,944,396, 4,543,190, 5,387,398, 5,405,533, 5,501,799, 5,560,822, 5,804,066, 6,054,057, 6,056,883, 6,238,568, 6,519,926, 6,576,185, 6,709,602, and 6,773,581, the disclosure of each of which is incorporated herein by reference in its entirety. In certain embodiments, the SCWO process is carried out in an InnovOx laboratory TOC Analyzer (GE Analytical Instruments, Inc., Boulder, Col.). Supercritical water oxidation (SCWO) processes take advantage of the unique properties of water at conditions near and beyond the thermodynamic critical point of water (375° C. and 218 atm). The increased pressure under supercritical water oxidation conditions dramatically increases the efficiency of the oxidation process by converting the organic carbon in the sodium nitrite-containing sample into carbon dioxide.

In certain embodiments, the sodium nitrite-containing sample solution is prepared by adding 5.0 g of a sodium nitrite-containing sample into water to make 100 mL solution. In certain embodiments, the water used in the method has total organic carbon of no greater than 0.10 ppm.

In certain embodiments, the method further comprises the step of determining the amount of carbon dioxide formed after oxidation. In certain embodiments, the carbon dioxide is quantitated using an infrared detector. In certain embodiments, the carbon dioxide is quantitated using a nondispersive infrared detector.

2. Quantitation of Nitrite and Nitrate in Sodium Nitrite

In certain embodiments, provided herein is a method of quantitating nitrite and nitrate in a sodium nitrite-containing sample, which comprises the steps of: (a) separating nitrite and nitrate by ion chromatography; and (b) quantitating the individual amounts of nitrite and nitrate using suppressed conductivity detection. In certain embodiments, the ion chromatography is performed isocratically. In certain embodiments, the aqueous mobile phase contains sodium carbonate and sodium bicarbonate. In certain embodiments, the aqueous mobile phase contains 2.7 mM sodium carbonate and 0.3 mM sodium bicarbonate.

3. Quantitation of Alkyl Naphthalene Sulfonates in Sodium Nitrite

In certain embodiments, provided herein is a method of quantitating alkyl naphthalene sulfonates in a sodium nitrite-containing sample, which comprises quantitating the alkyl naphthalene sulfonates with mass spectrometer and liquid chromatography.

4. Quantitation of Nitrogen Oxide Impurities in Sodium Nitrite

In certain embodiments, provided herein is a method of quantitating nitrogen oxide impurities in a sodium nitrite-containing sample, which comprises quantitating the nitrogen oxide impurities using nitrogen oxide ($NO_x$) electrode.

Pharmaceutical Compositions

Provided herein are pharmaceutical compositions comprising the sodium nitrite provided herein as an active ingredient, alone or in combination with a pharmaceutically acceptable vehicle, carrier, diluent, or excipient, or a mixture thereof.

The compound provided herein may be administered alone, or in combination with one or more other active ingredients. The pharmaceutical compositions that comprise the sodium nitrite provided herein may be formulated in various dosage forms for oral, parenteral, and topical administration. The pharmaceutical compositions may also be formulated as modified release dosage forms, including delayed-, extended-, prolonged-, sustained-, pulsatile-, controlled-, accelerated- and fast-, targeted-, programmed-release, and gastric retention dosage forms. These dosage forms can be prepared according to conventional methods and techniques known to those skilled in the art (see, *Remington: The Science and Practice of Pharmacy*, supra; *Modified-Release Drug Deliver Technology*, Rathbone et al., Eds., Drugs and the Pharmaceutical Science, Marcel Dekker, Inc.: New York, N.Y., 2003; Vol. 126).

In one embodiment, the pharmaceutical compositions are provided in a dosage form for oral administration, which comprise the sodium nitrite provided herein, and one or more pharmaceutically acceptable excipients or carriers.

In another embodiment, the pharmaceutical compositions are provided in a dosage form for parenteral administration, which comprise the sodium nitrite provided herein, and one or more pharmaceutically acceptable excipients or carriers.

In yet another embodiment, the pharmaceutical compositions are provided in a dosage form for topical administration, including pulmonary administration, which comprise the sodium nitrite provided herein, and one or more pharmaceutically acceptable excipients or carriers.

In one embodiment, the pharmaceutical composition comprises sodium nitrite provided herein and water. In another embodiment, the pharmaceutical composition comprises about 300 mg of sodium nitrite provided herein in about 10 mL of water.

In one embodiment, the pharmaceutical composition provided herein further comprises an acid. In certain embodiments, the acid is an organic acid. In certain embodiments, the acid is an inorganic acid. In certain embodiments, the acid is acetic acid or ascorbic acid. In certain embodiments, the sodium nitrite and the acid the pharmaceutical composition provided herein are mixed together when the composition is administered to a subject. In certain embodiments, the pharmaceutical composition provided herein is administered in or through a medical instrument or device (See, U.S. Pat. App. Publ. No. 2007/0239107, the disclosure of which is incorporated herein by reference in its entirety).

In certain embodiments, the sodium nitrite in pharmaceutical composition provided herein is not acidified (e.g., non-acidified).

The pharmaceutical compositions provided herein may be provided in a unit-dosage form or multiple-dosage form. A unit-dosage form, as used herein, refers to a physically discrete unit suitable for administration to a human and animal subject, and packaged individually as is known in the art. Each unit-dose contains a predetermined quantity of the active ingredient(s) sufficient to produce the desired therapeutic effect, in association with the required pharmaceutical carriers or excipients. Examples of a unit-dosage form include an ampoule, syringe, and individually packaged tablet or capsule. A unit-dosage form may be administered in fractions or multiples thereof. A multiple-dosage form is a plurality of identical unit-dosage forms packaged in a single container to be administered in segregated unit-dosage form. Examples of a multiple-dosage form include a vial, bottle of tablets or capsules, or bottle of pints or gallons.

The pharmaceutical compositions provided herein may be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

A. Oral Administration

The pharmaceutical compositions provided herein may be provided in solid, semisolid, or liquid dosage forms for oral administration. As used herein, oral administration also includes buccal, lingual, and sublingual administration. Suitable oral dosage forms include, but are not limited to, tablets, capsules, pills, troches, lozenges, pastilles, cachets, pellets, medicated chewing gum, granules, bulk powders, effervescent or non-effervescent powders or granules, solutions, emulsions, suspensions, solutions, wafers, sprinkles, elixirs, and syrups. In addition to the active ingredient(s), the pharmaceutical compositions may contain one or more pharmaceutically acceptable carriers or excipients, including, but not limited to, binders, fillers, diluents, disintegrants, wetting agents, lubricants, glidants, coloring agents, dye-migration inhibitors, sweetening agents, and flavoring agents.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. The binder or filler may be present from about 50 to about 99% by weight in the pharmaceutical compositions provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of a disintegrant in the pharmaceutical compositions provided herein varies upon the type of formulation, and is readily discernible to those of ordinary skill in the art. The pharmaceutical compositions provided herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W.R. Grace Co., Baltimore, Md.) and CAB-O-SIL® (Cabot Co. of Boston, Mass.); and mixtures thereof. The pharmaceutical compositions provided herein may contain about 0.1 to about 5% by weight of a lubricant.

Suitable glidants include colloidal silicon dioxide, CAB-O-SIL® (Cabot Co. of Boston, Mass.), and asbestos-free talc. Coloring agents include any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Flavoring agents include natural flavors extracted from plants, such as fruits, and synthetic blends of compounds which produce a pleasant taste sensation, such as peppermint and methyl salicylate. Sweetening agents include sucrose, lactose, mannitol, syrups, glycerin, and artificial sweeteners, such as saccharin and aspartame. Suitable emulsifying agents include gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suspending and dispersing agents include sodium carboxymethylcellulose, pectin, tragacanth, Veegum, acacia, sodium carbomethylcellulose, hydroxypropyl methylcellulose, and polyvinylpyrrolidone. Preservatives include glycerin, methyl and propylparaben, benzoic add, sodium benzoate and alcohol. Wetting agents include propylene glycol monostearate, sorbitan monooleate, diethylene glycol monolaurate, and polyoxyethylene lauryl ether. Solvents include glycerin, sorbitol, ethyl alcohol, and syrup. Examples of non-aqueous liquids utilized in emulsions include mineral oil and cottonseed oil. Organic acids include citric and tartaric acid. Sources of carbon dioxide include sodium bicarbonate and sodium carbonate.

It should be understood that many carriers and excipients may serve several functions, even within the same formulation.

The pharmaceutical compositions provided herein may be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms may be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein may be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

The pharmaceutical compositions provided herein may be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquid or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations may further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfate, sodium metabisulfite, thiodipropionic acid and its esters, and dithiocarbamates.

The pharmaceutical compositions provided herein for oral administration may be also provided in the forms of liposomes, micelles, microspheres, or nanosystems. Micellar dosage forms can be prepared as described in U.S. Pat. No. 6,350,458.

The pharmaceutical compositions provided herein may be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

The pharmaceutical compositions provided herein may be formulated as immediate or modified release dosage forms, including delayed-, sustained, pulsed-, controlled, targeted-, and programmed-release forms.

The pharmaceutical compositions provided herein may be co-formulated with other active ingredients which do not impair the desired therapeutic action, or with substances that supplement the desired action.

B. Parenteral Administration

The pharmaceutical compositions provided herein may be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, intravesical, and subcutaneous administration.

The pharmaceutical compositions provided herein may be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, *Remington: The Science and Practice of Pharmacy*, supra).

The pharmaceutical compositions intended for parenteral administration may include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfate and sodium metabisulfite. Suitable local anesthetics include, but are not limited to, procaine hydrochloride. Suitable suspending and dispersing agents are those as described herein, including sodium carboxymethylcelluose, hydroxypropyl methylcellulose, and polyvinylpyrrolidone. Suitable emulsifying agents include those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kan.).

The pharmaceutical compositions provided herein may be formulated for single or multiple dosage administration. The single dosage formulations are packaged in an ampoule, a vial, or a syringe. The multiple dosage parenteral formulations must contain an antimicrobial agent at bacteriostatic or fungistatic concentrations. All parenteral formulations must be sterile, as known and practiced in the art.

In one embodiment, the pharmaceutical compositions are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions provided herein may be formulated as immediate or modified release dosage forms, including delayed-, sustained-, pulsed-, controlled, targeted-, and programmed-release forms.

The pharmaceutical compositions may be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions to diffuse through.

Suitable inner matrixes include polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

Suitable outer polymeric membranes include polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

C. Topical Administration

The pharmaceutical compositions provided herein may be administered topically to the skin, orifices, or mucosa. The topical administration, as used herein, includes (intra)dermal, conjunctival, intracorneal, intraocular, ophthalmic, auricular, transdermal, nasal, vaginal, urethral, respiratory, and rectal administration.

The pharmaceutical compositions provided herein may be formulated in any dosage forms that are suitable for topical administration for local or systemic effect, including emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, dermal patches. The topical formulation of the pharmaceutical compositions provided herein may also comprise liposomes, micelles, microspheres, nanosystems, and mixtures thereof.

Pharmaceutically acceptable carriers and excipients suitable for use in the topical formulations provided herein include, but are not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryoprotectants, lyoprotectants, thickening agents, and inert gases.

The pharmaceutical compositions may also be administered topically by electroporation, iontophoresis, phonophoresis, sonophoresis, or microneedle or needle-free injection, such as POWDERJECT™ (Chiron Corp., Emeryville, Calif.), and BIOJECT™ (Bioject Medical Technologies Inc., Tualatin, Oreg.).

The pharmaceutical compositions provided herein may be provided in the forms of ointments, creams, and gels. Suitable ointment vehicles include oleaginous or hydrocarbon vehicles, including lard, benzoinated lard, olive oil, cottonseed oil, and other oils, white petrolatum; emulsifiable or absorption vehicles, such as hydrophilic petrolatum, hydroxystearin sulfate, and anhydrous lanolin; water-removable vehicles, such as hydrophilic ointment; water-soluble ointment vehicles, including polyethylene glycols of varying molecular weight; emulsion vehicles, either water-in-oil (W/O) emulsions or oil-in-water (O/W) emulsions, including cetyl alcohol, glyceryl monostearate, lanolin, and stearic acid (see, *Remington: The Science and Practice of Pharmacy*, supra). These vehicles are emollient but generally require addition of antioxidants and preservatives.

Suitable cream base can be oil-in-water or water-in-oil. Cream vehicles may be water-washable, and contain an oil phase, an emulsifier, and an aqueous phase. The oil phase is also called the "internal" phase, which is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation may be a nonionic, anionic, cationic, or amphoteric surfactant.

Gels are semisolid, suspension-type systems. Single-phase gels contain organic macromolecules distributed substantially uniformly throughout the liquid carrier. Suitable gelling agents include crosslinked acrylic acid polymers, such as carbomers, carboxypolyalkylenes, CARBOPOL®; hydrophilic polymers, such as polyethylene oxides, polyoxyethylene-polyoxypropylene copolymers, and polyvinylalcohol; cellulosic polymers, such as hydroxypropyl cellulose, hydroxyethyl cellulose, hydroxypropyl methylcellulose, hydroxypropyl methylcellulose phthalate, and methylcellulose; gums, such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

The pharmaceutical compositions provided herein may be administered rectally, urethrally, vaginally, or perivaginally in the forms of suppositories, pessaries, bougies, poultices or cataplasm, pastes, powders, dressings, creams, plasters, contraceptives, ointments, solutions, emulsions, suspensions, tampons, gels, foams, sprays, or enemas. These dosage forms can be manufactured using conventional processes as described in *Remington: The Science and Practice of Pharmacy*, supra.

Rectal, urethral, and vaginal suppositories are solid bodies for insertion into body orifices, which are solid at ordinary temperatures but melt or soften at body temperature to release the active ingredient(s) inside the orifices. Pharmaceutically acceptable carriers utilized in rectal and vaginal suppositories include bases or vehicles, such as stiffening agents, which produce a melting point in the proximity of body temperature, when formulated with the pharmaceutical compositions provided herein; and antioxidants as described herein, including bisulfite and sodium metabisulfite. Suitable vehicles include, but are not limited to, cocoa butter (theobroma oil), glycerin-gelatin, carbowax (polyoxyethylene glycol), spermaceti, paraffin, white and yellow wax, and appropriate mixtures of mono-, di- and triglycerides of fatty acids, hydrogels, such as polyvinyl alcohol, hydroxyethyl methacrylate, polyacrylic acid; glycerinated gelatin. Combinations of the various vehicles may be used. Rectal and vaginal suppositories may be prepared by the compressed method or molding. The typical weight of a rectal and vaginal suppository is about 2 to about 3 g.

The pharmaceutical compositions provided herein may be administered ophthalmically in the forms of solutions, suspensions, ointments, emulsions, gel-forming solutions, powders for solutions, gels, ocular inserts, and implants.

The pharmaceutical compositions provided herein may be administered intranasally or by inhalation to the respiratory tract. The pharmaceutical compositions may be provided in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. The pharmaceutical compositions may also be provided as a dry powder for insufflation, alone or in combination with an inert carrier such as lactose or phospholipids; and nasal drops. For intranasal use, the powder may comprise a bioadhesive agent, including chitosan or cyclodextrin.

Solutions or suspensions for use in a pressurized container, pump, spray, atomizer, or nebulizer may be formulated to contain ethanol, aqueous ethanol, or a suitable alternative agent for dispersing, solubilizing, or extending release of the active ingredient provided herein, a propellant as solvent; and/or a surfactant, such as sorbitan trioleate, oleic acid, or an oligolactic acid.

The pharmaceutical compositions provided herein may be micronized to a size suitable for delivery by inhalation, such as about 50 micrometers or less, or about 10 micrometers or less. Particles of such sizes may be prepared using a comminuting method known to those skilled in the art, such as spiral jet milling, fluid bed jet milling, supercritical fluid processing to form nanoparticles, high pressure homogenization, or spray drying.

Capsules, blisters and cartridges for use in an inhaler or insufflator may be formulated to contain a powder mix of the pharmaceutical compositions provided herein; a suitable powder base, such as lactose or starch; and a performance modifier, such as l-leucine, mannitol, or magnesium stearate. The lactose may be anhydrous or in the form of the monohydrate. Other suitable excipients or carriers include dextran, glucose, maltose, sorbitol, xylitol, fructose, sucrose, and trehalose. The pharmaceutical compositions provided herein for inhaled/intranasal administration may further comprise a suitable flavor, such as menthol and levomenthol, or sweeteners, such as saccharin or saccharin sodium.

The pharmaceutical compositions provided herein for topical administration may be formulated to be immediate release or modified release, including delayed-, sustained-, pulsed-, controlled-, targeted, and programmed release.

D. Modified Release

The pharmaceutical compositions provided herein may be formulated as a modified release dosage form. As used herein, the term "modified release" refers to a dosage form in which the rate or place of release of the active ingredient(s) is different from that of an immediate dosage form when administered by the same route. Modified release dosage forms include delayed-, extended-, prolonged-, sustained-, pulsatile-, controlled-, accelerated- and fast-, targeted-, programmed-release, and gastric retention dosage forms. The pharmaceutical compositions in modified release dosage forms can be prepared using a variety of modified release devices and methods known to those skilled in the art, including, but not limited to, matrix controlled release devices, osmotic controlled release devices, multiparticulate controlled release devices, ion-exchange resins, enteric coatings, multilayered coatings, microspheres, liposomes, and combinations thereof. The release rate of the active ingredient(s) can also be modified by varying the particle sizes and polymorphism of the active ingredient(s).

Examples of modified release include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; and 6,699,500.

1. Matrix Controlled Release Devices

The pharmaceutical compositions provided herein in a modified release dosage form may be fabricated using a matrix controlled release device known to those skilled in the art (see, Takada et al in "Encyclopedia of Controlled Drug Delivery," Vol. 2, Mathiowitz Ed., Wiley, 1999).

In one embodiment, the pharmaceutical compositions provided herein in a modified release dosage form is formulated using an erodible matrix device, which is water-swellable, erodible, or soluble polymers, including synthetic polymers, and naturally occurring polymers and derivatives, such as polysaccharides and proteins.

Materials useful in forming an erodible matrix include, but are not limited to, chitin, chitosan, dextran, and pullulan; gum agar, gum arabic, gum karaya, locust bean gum, gum tragacanth, carrageenans, gum ghatti, guar gum, xanthan gum, and scleroglucan; starches, such as dextrin and maltodextrin; hydrophilic colloids, such as pectin; phosphatides, such as lecithin; alginates; propylene glycol alginate; gelatin; collagen; and cellulosics, such as ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethylhydroxy ethylcellulose (EHEC); polyvinyl pyrrolidone; polyvinyl alcohol; polyvinyl acetate; glycerol fatty acid esters; polyacrylamide; polyacrylic acid; copolymers of ethacrylic acid or methacrylic acid (EUDRAGIT®, Rohm America, Inc., Piscataway, N.J.); poly(2-hydroxyethyl-methacrylate); polylactides; copolymers of L-glutamic acid and ethyl-L-glutamate; degradable lactic acid-glycolic acid copolymers; poly-D-(−)-3-hydroxybutyric acid; and other acrylic acid derivatives, such as homopolymers and copolymers of butylmethacrylate, methylmethacrylate, ethylmethacrylate, ethylacrylate, (2-dimethylaminoethyl)methacrylate, and (trimethylaminoethyl)methacrylate chloride.

In further embodiments, the pharmaceutical compositions are formulated with a non-erodible matrix device. The active ingredient(s) is dissolved or dispersed in an inert matrix and is released primarily by diffusion through the inert matrix once administered. Materials suitable for use as a non-erodible matrix device included, but are not limited to, insoluble plastics, such as polyethylene, polypropylene, polyisoprene, polyisobutylene, polybutadiene, polymethylmethacrylate, polybutylmethacrylate, chlorinated polyethylene, polyvinylchloride, methyl acrylate-methyl methacrylate copolymers, ethylene-vinyl acetate copolymers, ethylene/propylene copolymers, ethylene/ethyl acrylate copolymers, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, polyvinyl chloride, plasticized nylon, plasticized polyethylene terephthalate, natural rubber, silicone rubbers, polydimethylsiloxanes, silicone carbonate copolymers, and; hydrophilic polymers, such as ethyl cellulose, cellulose acetate, crospovidone, and cross-linked partially hydrolyzed polyvinyl acetate; and fatty compounds, such as carnauba wax, microcrystalline wax, and triglycerides.

In a matrix controlled release system, the desired release kinetics can be controlled, for example, via the polymer type employed, the polymer viscosity, the particle sizes of the polymer and/or the active ingredient(s), the ratio of the active ingredient(s) versus the polymer, and other excipients or carriers in the compositions.

The pharmaceutical compositions provided herein in a modified release dosage form may be prepared by methods known to those skilled in the art, including direct compression, dry or wet granulation followed by compression, melt-granulation followed by compression.

2. Osmotic Controlled Release Devices

The pharmaceutical compositions provided herein in a modified release dosage form may be fabricated using an osmotic controlled release device, including one-chamber system, two-chamber system, asymmetric membrane technology (AMT), and extruding core system (ECS). In general, such devices have at least two components: (a) the core which contains the active ingredient(s); and (b) a semipermeable membrane with at least one delivery port, which encapsulates the core. The semipermeable membrane controls the influx of water to the core from an aqueous environment of use so as to cause drug release by extrusion through the delivery port(s).

In addition to the active ingredient(s), the core of the osmotic device optionally includes an osmotic agent, which creates a driving force for transport of water from the environment of use into the core of the device. One class of osmotic agents water-swellable hydrophilic polymers, which are also referred to as "osmopolymers" and "hydrogels," including, but not limited to, hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly(acrylic) acid, poly(methacrylic) acid, polyvinylpyrrolidone (PVP), crosslinked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

The other class of osmotic agents is osmogens, which are capable of imbibing water to affect an osmotic pressure gradient across the barrier of the surrounding coating. Suitable osmogens include, but are not limited to, inorganic salts, such as magnesium sulfate, magnesium chloride, calcium chloride, sodium chloride, lithium chloride, potassium sulfate, potassium phosphates, sodium carbonate, sodium sulfite, lithium sulfate, potassium chloride, and sodium sulfate; sugars, such as dextrose, fructose, glucose, inositol, lactose, maltose, mannitol, raffinose, sorbitol, sucrose, trehalose, and xylitol; organic acids, such as ascorbic acid, benzoic acid, fumaric acid, citric acid, maleic acid, sebacic acid, sorbic acid, adipic acid, edetic acid, glutamic acid, p-toluenesulfonic acid, succinic acid, and tartaric acid; urea; and mixtures thereof.

Osmotic agents of different dissolution rates may be employed to influence how rapidly the active ingredient(s) is initially delivered from the dosage form. For example, amorphous sugars, such as MANNOGEM™ EZ (SPI Pharma, Lewes, Del.) can be used to provide faster delivery during the first couple of hours to promptly produce the desired therapeutic effect, and gradually and continually release of the remaining amount to maintain the desired level of therapeutic or prophylactic effect over an extended period of time. In this case, the active ingredient(s) is released at such a rate to replace the amount of the active ingredient metabolized and excreted.

The core may also include a wide variety of other excipients and carriers as described herein to enhance the performance of the dosage form or to promote stability or processing.

Materials useful in forming the semipermeable membrane include various grades of acrylics, vinyls, ethers, polyamides, polyesters, and cellulosic derivatives that are water-permeable and water-insoluble at physiologically relevant pHs, or are susceptible to being rendered water-insoluble by chemical alteration, such as crosslinking. Examples of suitable polymers useful in forming the coating, include plasticized, unplasticized, and reinforced cellulose acetate (CA), cellulose diacetate, cellulose triacetate, CA propionate, cellulose nitrate, cellulose acetate butyrate (CAB), CA ethyl carbamate, CAP, CA methyl carbamate, CA succinate, cellulose acetate trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxylated ethylene-vinylacetate, EC, PEG, PPG, PEG/PPG copolymers, PVP, HEC, HPC, CMC, CMEC, HPMC, HPMCP, HPMCAS, HPMCAT, poly(acrylic) acids and esters and poly-(methacrylic) acids and esters and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural waxes, and synthetic waxes.

Semipermeable membrane may also be a hydrophobic microporous membrane, wherein the pores are substantially filled with a gas and are not wetted by the aqueous medium but are permeable to water vapor, as disclosed in U.S. Pat. No. 5,798,119. Such hydrophobic but water-vapor permeable membrane are typically composed of hydrophobic polymers such as polyalkenes, polyethylene, polypropylene, polytetrafluoroethylene, polyacrylic acid derivatives, polyethers, polysulfones, polyethersulfones, polystyrenes, polyvinyl halides, polyvinylidene fluoride, polyvinyl esters and ethers, natural waxes, and synthetic waxes.

The delivery port(s) on the semipermeable membrane may be formed post-coating by mechanical or laser drilling. Delivery port(s) may also be formed in situ by erosion of a plug of water-soluble material or by rupture of a thinner portion of the membrane over an indentation in the core. In addition, delivery ports may be formed during coating process, as in the case of asymmetric membrane coatings of the type disclosed in U.S. Pat. Nos. 5,612,059 and 5,698,220.

The total amount of the active ingredient(s) released and the release rate can substantially by modulated via the thickness and porosity of the semipermeable membrane, the composition of the core, and the number, size, and position of the delivery ports.

The pharmaceutical compositions in an osmotic controlled-release dosage form may further comprise additional conventional excipients or carriers as described herein to promote performance or processing of the formulation.

The osmotic controlled-release dosage forms can be prepared according to conventional methods and techniques known to those skilled in the art (see, *Remington: The Science and Practice of Pharmacy*, supra; Santus and Baker, *J. Controlled Release* 1995, 35, 1-21; Verma et al., *Drug Development and Industrial Pharmacy* 2000, 26, 695-708; Verma et al., *J. Controlled Release* 2002, 79, 7-27).

In certain embodiments, the pharmaceutical compositions provided herein are formulated as AMT controlled-release dosage form, which comprises an asymmetric osmotic membrane that coats a core comprising the active ingredient(s) and other pharmaceutically acceptable excipients or carriers. See, U.S. Pat. No. 5,612,059 and WO 2002/17918. The AMT controlled-release dosage forms can be prepared according to conventional methods and techniques known to those skilled in the art, including direct compression, dry granulation, wet granulation, and a dip-coating method.

In certain embodiments, the pharmaceutical compositions provided herein are formulated as ESC controlled-release dosage form, which comprises an osmotic membrane that coats a core comprising the active ingredient(s), a hydroxylethyl cellulose, and other pharmaceutically acceptable excipients or carriers.

3. Multiparticulate Controlled Release Devices

The pharmaceutical compositions provided herein in a modified release dosage form may be fabricated as a multiparticulate controlled release device, which comprises a multiplicity of particles, granules, or pellets, ranging from about 10 μm to about 3 mm, about 50 μm to about 2.5 mm, or from about 100 μm to about 1 mm in diameter. Such multiparticulates may be made by the processes known to those skilled in the art, including wet- and dry-granulation, extrusion/spheronization, roller-compaction, melt-congealing, and by spray-coating seed cores. See, for example, *Multiparticulate Oral Drug Delivery*; Marcel Dekker: 1994; and *Pharmaceutical Pelletization Technology*; Marcel Dekker: 1989.

Other excipients or carriers as described herein may be blended with the pharmaceutical compositions to aid in processing and forming the multiparticulates. The resulting particles may themselves constitute the multiparticulate device or may be coated by various film-forming materials, such as enteric polymers, water-swellable, and water-soluble polymers. The multiparticulates can be further processed as a capsule or a tablet.

4. Targeted Delivery

The pharmaceutical compositions provided herein may also be formulated to be targeted to a particular tissue, receptor, or other area of the body of the subject to be treated, including liposome-, resealed erythrocyte-, and antibody-based delivery systems. Examples include, but are not limited to, U.S. Pat. Nos. 6,316,652; 6,274,552; 6,271,359; 6,253,872; 6,139,865; 6,131,570; 6,120,751; 6,071,495; 6,060,082; 6,048,736; 6,039,975; 6,004,534; 5,985,307; 5,972,366; 5,900,252; 5,840,674; 5,759,542; and 5,709,874.

Methods of Use

In one embodiment, provided herein are methods for treating a cyanide poisoning, which comprises administering to a subject a therapeutically effective amount of sodium nitrite provided herein. In one embodiment, the subject is a mammal. In another embodiment, the subject is a human. In certain embodiments, the method further comprises the administration to the subject a therapeutically effective amount of sodium thiosulfate (e.g., sodium thiosulfate pentahydrate). In certain embodiments, the method further comprises the administration to the subject a therapeutically effective amount of pharmaceutical grade sodium thiosulfate (e.g., pharmaceutical grade sodium thiosulfate pentahydrate). Suitable forms of and methods for making pharmaceutical-grade sodium thiosulfate for co-administration with sodium nitrite are provided in U.S. Provisional Application No. 61/223,993, filed on Jul. 8, 2009, titled SODIUM THIOSULFATE-CONTAINING PHARMACEUTICAL COMPOSITIONS, which is incorporated by reference herein in its entirety, as well as in Example 6 set forth herein. In certain embodiments, pharmaceutical grade sodium thiosulfate is characterized by one or more of the following:

containing no less than about 99% by weight and/or no greater than about 100.5% by weight of sodium thiosulfate on an anhydrous basis;

having a pH between about 6 to about 8 when measured in a 10% solution at 25° C.;

having water content of about 32% to about 37% by weight;

having an appearance of colorless crystals;

having a clear and colorless appearance as a 10% solution;

having no odor;

having a positive identification test for sodium;

having a positive identification test for thiosulfate;

having no turbidy when mixed with ammonium oxalate TS;

having heavy metal content of no greater than about 10 ppm;

containing no greater than about 0.01% by weight of carbonate;

containing no greater than about 0.005% by weight of insoluble matter;

containing no greater than about 200 ppm of chloride;

containing no greater than about 0.001% by weight of sulfide;

containing no greater than about 0.05% or no greater than about 0.1% by weight of sulfite;

containing no greater than about 0.05%, no greater than about 0.1%, no greater than about 0.25%, or no greater than about 0.5% by weight of sulfate;

containing no greater than about 0.002% by weight of iron;

containing no greater than about 0.01% by weight of calcium;

containing no greater than about 0.005% by weight of potassium;

containing no greater than about 10 ppm, no greater than about 100 ppm, no greater than about 500 ppm, no greater than about 1000 ppm, or no greater than 5000 ppm of organic volatile impurities;

having total NVOC or NPOC of no greater than 60 ppb, no greater than about 2.5 ppm, no greater than about 8 ppm, no greater than about 10 ppm, no greater than about 20 ppm, no greater than about 25 ppm, or no greater than about 50 ppm;

containing no greater than about 0.05 ppm of mercury;

containing no greater than about 2 ppm of aluminum;

containing no greater than about 3 ppm of arsenic;

containing no greater than 0.001% by weight of lead;

containing no greater than about 0.002% by weight of nitrogen compounds (as N);

containing no greater than about 0.003% by weight of selenium; having a total aerobic count of microbial load of no greater than about 100 CFU/g;

having a total yeast and mold count of no greater than about 20 CFU/g; and containing no greater than about 0.02 EU/mg, no greater than about 0.1 EU/mg, or no greater than about 0.25 EU/mg of bacterial endotoxins.

In certain embodiments, the sodium nitrite administered to the subject is not acidified.

In another embodiment, provided herein are methods for treating a hydrogen sulfide poisoning, which comprises administering to a subject a therapeutically effective amount of sodium nitrite provided herein. In one embodiment, the subject is a mammal. In another embodiment, the subject is a human. In certain embodiments, the sodium nitrite administered to the subject is not acidified.

In yet another embodiment, provided herein is a method for treating a cardiovascular disease or a condition associated with the cardiovascular system, including, but not limited to, high blood pressure, pulmonary hypertension, cerebral vasospasm, angina, claudication, peripheral artery disease, critical limb ischemia and tissue ischemia-reperfusion injury, which comprises administering to a subject a therapeutically effective amount of sodium nitrite provided herein. In one embodiment, the subject is a mammal. In another embodiment, the subject is a human. In certain embodiments, the sodium nitrite administered to the subject is not acidified.

In certain embodiments, the condition associated with the cardiovascular system is one or more of pulmonary hypertension (e.g., neonatal pulmonary hypertension, primary pulmonary hypertension, and secondary pulmonary hypertension), systemic hypertension, cutaneous ulceration, acute renal failure, chronic renal failure, intravascular thrombosis, and an ischemic central nervous system event.

In yet another embodiment, provided herein is a method for treating a condition associated with elevated blood pressure, which comprises administering to a subject a therapeutically effective amount of sodium nitrite provided herein. In one embodiment, the subject is a mammal. In another embodiment, the subject is a human. In certain embodiments, the sodium nitrite administered to the subject is not acidified.

In yet another embodiment, provided herein is a method for increasing blood flow to tissues, for example, to tissues in regions of low oxygen tension, which comprises administering to a subject a therapeutically effective amount of sodium nitrite provided herein. In one embodiment, the subject is a mammal. In another embodiment, the subject is a human. In certain embodiments, the sodium nitrite administered to the subject is not acidified.

In yet another embodiment, provided herein is a method for stimulating the growth of new blood vessels, for example, within tissues in regions of poor circulation and low oxygen tension, which comprises administering to a subject a therapeutically effective amount of sodium nitrite provided herein. In one embodiment, the subject is a mammal. In another embodiment, the subject is a human. In certain embodiments, the sodium nitrite administered to the subject is not acidified.

In certain embodiments, the decreased blood flow to the tissue is caused directly or indirectly by at least one of the following conditions: sickle cell anemia, thalassemia, hemoglobin C disease, hemoglobin SC disease, sickle thalassemia, hereditary spherocytosis, hereditary elliptocytosis, hereditary ovalcytosis, glucose-6-phosphate deficiency and other red blood cell enzyme deficiencies, paroxysmal nocturnal hemoglobinuria (PNH), paroxysmal cold hemoglobinuria (PCH), thrombotic thrombocytopenic purpura/hemolytic uremic syndrome (TTP/HUS), idiopathic autoimmune hemolytic anemia, drug-induced immune hemolytic anemia, secondary immune hemolytic anemia, non-immune hemolytic anemia caused by chemical or physical agents, malaria, falciparum malaria, bartonellosis, babesiosis, clostridial infection, severe haemophilus influenzae type b infection, extensive burns, transfusion reaction, rhabdomyolysis (myoglobinemia), transfusion of aged blood, transfusion of hemoglobin, transfusion of red blood cells, cardiopulmonary bypass, coronary disease, cardiac ischemia syndrome, angina, iatrogenic hemolysis, angioplasty, myocardial ischemia, tissue ischemia, hemolysis caused by intravascular devices, hemodialysis, pulmonary hypertension, systemic hypertension, cutaneous ulceration, acute renal failure, chronic renal failure, intravascular thrombosis, and an ischemic central nervous system event. In certain embodiments, the tissue is an ischemic tissue.

In yet another embodiment, provided herein is a method for treating hemolytic condition, which comprises administering to a subject a therapeutically effective amount of sodium nitrite provided herein. In one embodiment, the subject is a mammal. In another embodiment, the subject is a human. In certain embodiments, the sodium nitrite administered to the subject is not acidified.

In certain embodiments, the hemolytic condition includes one or more of sickle cell anemia, thalassemia, hemoglobin C disease, hemoglobin SC disease, sickle thalassemia, hereditary spherocytosis, hereditary elliptocytosis, hereditary ovalcytosis, glucose-6-phosphate deficiency and other red blood cell enzyme deficiencies, paroxysmal nocturnal hemoglobinuria (PNH), paroxysmal cold hemoglobinuria (PCH), thrombotic thrombocytopenic purpura/hemolytic uremic syndrome (TTP/HTJS), idiopathic autoimmune hemolytic anemia, drug-induced immune hemolytic anemia, secondary immune hemolytic anemia, non-immune hemolytic anemia caused by chemical or physical agents, malaria, falciparum malaria, bartonellosis, babesiosis, clostridial infection, severe haemophilus influenzae type b infection, extensive burns, transfusion reaction, rhabdomyolysis (myoglobinemia}, transfusion of aged blood, cardiopulomonary bypass, and hemodialysis.

In yet another embodiment, provided herein are methods for treating a respiratory disease or a condition associated with the tracheo-pulmonary system, including, but not limited to, cystic fibrosis, pulmonary tuberculosis, mycotic pneumonia, bacterial pneumonia, viral pneumonia, pulmonary abscess, pulmonary hypertension, pulmonary embolism, and pulmonary vasospasm, which comprises administering to a subject a therapeutically effective amount of sodium nitrite provided herein.

In yet another embodiment, provided herein are methods for treating a dermatological disease or a condition associated with the skin, including, but not limited to, bacterial infection of the skin, mycotic infection of the skin, viral infection of the skin, mycotic infection of the nails, bacterial infection of the nails, viral infection of the nails, mycotic infection of the nailbeds, bacterial infection of the nailbeds, viral infection of the nailbeds, psoriasis, scleroderma, inflammation of the skin, inflammation of the nails, and inflammation of the nailbeds, which comprises administering to a subject a therapeutically effective amount of sodium nitrite provided herein.

In still another embodiment, provided herein are methods for treating, preventing or reducing the risk of hospital-acquired infections, such as nocosomial infections, which can originate from the insertion of a device (e.g., a medical device) and/or the use of a device in the body. In one embodiment, the infection is caused by or associated with *S. aureus*. Such uses and devices are set forth in U.S. Patent Application Publication No. 2007/0239107, the disclosure of which is incorporated herein by reference in its entirety. Examples of such devices include, but are not limited to, urinary catheters, intratracheal tubes, vascular catheters, vascular catheter ports, wound drain tubes, gastric tubes. In certain embodiments, the sodium nitrite administered to the subject is acidified or administered in combination with an acidifying agent (e.g., and acid).

In certain embodiments, provided herein are methods for the preparation or manufacture of a medicament for the treatment, prevention or management of a disease or disorder provided herein, or a symptom thereof.

Depending on the condition, disorder, or disease, to be treated and the subject's condition, the sodium nitrite provided herein may be administered by oral, parenteral (e.g., intramuscular, intraperitoneal, intravenous, ICV, intracistemal injection or infusion, subcutaneous injection, or implant), inhalation, nasal, vaginal, rectal, sublingual, or topical (e.g., transdermal or local) routes of administration, and may be formulated, alone or together, in suitable dosage unit with pharmaceutically acceptable carriers, adjuvants and vehicles appropriate for each route of administration.

The dose may be in the form of one, two, three, four, five, six, or more sub-doses that are administered at appropriate intervals per day. The dose or sub-doses can be administered in the form of dosage units containing from about 10 ng to about 1000 mg, from about 20 ng to about 5 mg, from about 50 ng to about 1 mg, from about 50 ng to about 0.2 mg, or from about 50 ng to about 0.5 mg active ingredient(s) per dosage unit, and if the condition of the patient requires, the dose can, by way of alternative, be administered as a continuous infusion.

In certain embodiments, an appropriate dosage level is about 0.01 to about 100 mg per kg patient body weight per day (mg/kg per day), about 0.01 to about 50 mg/kg per day, about 0.01 to about 25 mg/kg per day, or about 0.05 to about 10 mg/kg per day, which may be administered in single or multiple doses. A suitable dosage level may be about 0.01 to about 100 mg/kg per day, about 0.05 to about 50 mg/kg per day, or about 0.1 to about 10 mg/kg per day. Within this range the dosage may be about 0.01 to about 0.1, about 0.1 to about 1.0, about 1.0 to about 10, or about 10 to about 50 mg/kg per day.

In certain embodiments of the methods provided herein, the therapeutically effective amount of sodium nitrite administered to the subject does not induce toxic levels of methemoglobin, and in many embodiments does not induce formation of clinically significant amounts of methemoglobin in the subject. In certain embodiments, the effective amount of sodium nitrite administered to the subject induces production in the subject of no greater than about 25%, no greater than about 20%, no greater than about 10%, no greater than about 8%, no greater than about 5%, no greater than about 3%, no greater than about 2%, no greater than about 1% methemoglobin.

In certain embodiments of the methods provided herein, the therapeutically effective amount of sodium nitrite is administered one or more times per day, per week, per month, per year or longer. In certain embodiments of the methods provided herein, the therapeutically effective amount of sodium nitrite is administered intermittently or chronically. In certain embodiments of the methods provided herein, the therapeutically effective amount of sodium nitrite is administered intermittently or continuously for one or more hours, days, weeks, months, years or longer.

Combination Therapy

The sodium nitrite provided herein may also be combined or used in combination with other therapeutic agents useful in the treatment and/or prevention of the diseases and conditions provided herein.

As used herein, the term "in combination" includes the use of more than one therapy (e.g., one or more prophylactic and/or therapeutic agents). However, the use of the term "in combination" does not restrict the order in which therapies (e.g., prophylactic and/or therapeutic agents) are administered to a subject with a disease or disorder. A first therapy (e.g., a prophylactic or therapeutic agent such as a compound provided herein) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to the subject. Triple therapy is also contemplated herein.

As used herein, the term "synergistic" includes a combination of the sodium nitrite provided herein and another therapy (e.g., a prophylactic or therapeutic agent) which has been or is currently being used to treat, prevent, or manage a disease or disorder, which is more effective than the additive effects of the therapies. A synergistic effect of a combination of therapies (e.g., a combination of prophylactic or therapeutic agents) permits the use of lower dosages of one or more of the therapies and/or less frequent administration of said therapies to a subject with a disorder. The ability to utilize lower dosages of a therapy (e.g., a prophylactic or therapeutic agent) and/or to administer said therapy less frequently reduces the toxicity associated with the administration of said therapy to a subject without reducing the efficacy of said therapy in the prevention or treatment of a disorder). In addition, a synergistic effect can result in improved efficacy of agents in the prevention or treatment of a disorder. Finally, a synergistic effect of a combination of therapies (e.g., a combination of prophylactic or therapeutic agents) may avoid or reduce adverse or unwanted side effects associated with the use of either therapy alone.

The sodium nitrite provided herein can be administered in combination or alternation with another therapeutic agent. In combination therapy, effective dosages of two or more agents are administered together, whereas in alternation or sequential-step therapy, an effective dosage of each agent is administered serially or sequentially. The dosages given will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

The compounds provided herein can be administered in combination with other classes of compounds, including, but not limited to, endothelin converting enzyme (ECE) inhibitors, such as phosphoramidon; thromboxane receptor antagonists, such as ifetroban; potassium channel openers; thrombin inhibitors, such as hirudin; growth factor inhibitors, such as modulators of PDGF activity; platelet activating factor (PAF) antagonists; anti-platelet agents, such as GPIIb/IIIa blockers (e.g., abciximab, eptifibatide, and tirofiban), P2Y(AC) antagonists (e.g., clopidogrel, ticlopidine and CS-747), and aspirin; anticoagulants, such as warfarin; low molecular weight heparins, such as enoxaparin; Factor VIIa Inhibitors and Factor Xa Inhibitors; renin inhibitors; neutral endopeptidase (NEP) inhibitors; vasopeptidase inhibitors (dual NEP-ACE inhibitors), such as omapatrilat and gemopatrilat; HMG CoA reductase inhibitors, such as pravastatin, lovastatin, atorvastatin, simvastatin, NK-104 (a.k.a. itavastatin, nisvastatin, or nisbastatin), and ZD-4522 (also known as rosuvastatin, atavastatin, or visastatin); squalene synthetase inhibitors; fibrates; bile acid sequestrants, such as questran; niacin; anti-atherosclerotic agents, such as ACAT inhibitors; MTP Inhibitors; calcium channel blockers, such as amlodipine besylate; potassium channel activators; alpha-adrenergic agents; beta-adrenergic agents, such as carvedilol and metoprolol; antiarrhythmic agents; diuretics, such as chlorothiazide, hydrochlorothiazide, flumethiazide, hydroflumethiazide, bendroflumethiazide, methylchlorothiazide, trichloromethiazide, polythiazide, benzothiazide, ethacrynic acid, ticrynafen, chlorthalidone, furosenide, muzolimine, bumetanide, triamterene, amiloride, and spironolactone; thrombolytic agents, such as tissue plasminogen activator (tPA), recombinant tPA, streptokinase, urokinase, prourokinase, and anisoylated plasminogen streptokinase activator complex (APSAC); anti-diabetic agents, such as biguanides (e.g., metformin), glucosidase inhibitors (e.g., acarbose), insulins, meglitinides (e.g., repaglinide), sulfonylureas (e.g., glimepiride, glyburide, and glipizide), thiozolidinediones (e.g., troglitazone, rosiglitazone, and pioglitazone), and PPAR-gamma agonists; mineralocorticoid receptor antagonists, such as spironolactone and eplerenone; growth hormone secretagogues; aP2 inhibitors; phosphodiesterase inhibitors, such as PDE III inhibitors (e.g., cilostazol) and PDE V inhibitors (e.g., sildenafil, tadalafil, and vardenafil); protein tyrosine kinase inhibitors; antiinflammatories; antiproliferatives, such as methotrexate, FK506 (tacrolimus), mycophenolate mofetil; chemotherapeutic agents; immunosuppressants; anticancer agents and cytotoxic agents (e.g., alkylating agents, such as nitrogen mustards, alkyl sulfonates, nitrosoureas, ethylenimines, and triazenes); antimetabolites, such as folate antagonists, purine analogues, and pyrimidine analogues; antibiotics, such as anthracyclines, bleomycins, mitomycin, dactinomycin, and plicamycin; enzymes, such as L-asparaginase; farnesyl-protein transferase inhibitors; hormonal agents, such as glucocorticoids (e.g., cortisone), estrogens/antiestrogens, androgens/antiandrogens, progestins, and luteinizing hormone-releasing hormone antagonists, and octreotide acetate; microtubule-disruptor agents, such as ecteinascidins; microtubule-stabilizing agents, such as pacitaxel, docetaxel, and epothilones A-F; plant-derived products, such as vinca alkaloids, epipodophyllotoxins, and taxanes; and topoisomerase inhibitors; prenyl-protein transferase inhibitors; and cyclosporins; steroids, such as prednisone and dexamethasone; cytotoxic drugs, such as azathioprine and cyclophosphamide; TNF-alpha inhibitors, such as tenidap; anti-TNF antibodies or soluble TNF receptor, such as etanercept, rapamycin, and leflunimide; cyclooxygenase-2 (COX-2) inhibitors, such as celecoxib and rofecoxib; and miscellaneous agents such as, sodium thiosulfate, hydroxyurea, procarbazine, mitotane, hexamethylmelamine, gold compounds, platinum coordination complexes, such as cisplatin, satraplatin, and carboplatin.

The sodium nitrite provided herein can also be provided as an article of manufacture using packaging materials well known to those of skill in the art. See, e.g., U.S. Pat. Nos. 5,323,907; 5,052,558; and 5,033,252. Examples of pharmaceutical packaging materials include, but are not limited to, blister packs, bottles, tubes, inhalers, pumps, bags, vials, containers, syringes, and any packaging material suitable for a selected formulation and intended mode of administration and treatment.

Provided herein also are kits which, when used by the medical practitioner, can simplify the administration of appropriate amounts of active ingredients to a subject. In certain embodiments, the kit provided herein includes a container and a dosage form of the sodium nitrite provided herein.

In certain embodiments, the kit includes a container comprising a dosage form of the sodium nitrite provided herein, in a container comprising one or more other therapeutic agent(s) described herein.

Kits provided herein can further include devices that are used to administer the active ingredients. Examples of such devices include, but are not limited to, syringes, needle-less injectors drip bags, patches, and inhalers. The kits provided herein can also include condoms for administration of the active ingredients.

Kits provided herein can further include pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: aqueous vehicles, including, but not limited to, Water for Injection USP, Sodium Chloride Injection, Ringer's Injection, Dextrose Injection, Dextrose and Sodium Chloride Injection, and Lactated Ringer's Injection; water-miscible vehicles, including, but not limited to, ethyl alcohol, polyethylene glycol, and polypropylene glycol; and non-aqueous vehicles, including, but not limited to, corn oil, cottonseed oil, peanut oil, sesame oil, ethyl oleate, isopropyl myristate, and benzyl benzoate.

The sodium nitrite can also be used in connection with a medical device. Illustrative medical devices are set forth in U.S. Patent Application Publication No. 2007/0239107, the disclosure of which is incorporated herein by reference in its entirety. Examples of such devices include, but are not limited to, urinary catheters, intratracheal tubes, vascular catheters, vascular catheter ports, wound drain tubes, gastric tubes. In these embodiments, the device can contain or be coated with the sodium nitrite provided herein. With respect to a urinary catheter, the sodium nitrite could be contained in the inflatable or expandable portion that is inserted into the subject, contained in the collection bag or contained in tubing associated with the device.

The disclosure will be further understood by the following non-limiting examples.

EXAMPLES

As used herein, the symbols and conventions used in these processes, schemes and examples, regardless of whether a particular abbreviation is specifically defined, are consistent with those used in the contemporary scientific literature, for example, the Journal of the American Chemical Society or the Journal of Biological Chemistry. Specifically, but without limitation, the following abbreviations may be used in the examples and throughout the specification: g (grams); mg (milligrams); mL (milliliters); µL, (microliters); mM (millimolar); µM (micromolar); mmol (millimoles); eq. (equivalent); hr or hrs (hours); min (minutes).

For all of the following examples, standard work-up and purification methods known to those skilled in the art can be utilized. Unless otherwise indicated, all temperatures are expressed in ° C. (degrees Centigrade). All reactions conducted at room temperature unless otherwise noted. Methodologies illustrated in the following examples are intended to exemplify the applicable chemistry through the use of specific examples and are not indicative of the scope of the Example 1

Preparation of Pharmaceutical Grade Sodium Nitrite

Under nitrogen, deionized water (18.3 L) was charged to an inerted 50 gallon reactor. 15 kilograms of non-pharmaceutical grade sodium nitrite was added to the reactor. The reactor was re-inerted with nitrogen. The mixture was slowly heated to 50° C. and then stirred for additional 10 min to form a clear solution.

The solution was cooled to 25° C. and transferred to a 55 gallon plastic drum. 60 grams of activated carbon was added to the drum and the solution was mixed for 30 minutes.

The contents of the drum were filtered and transferred into the 50 gallon reactor. The 50 gallon reactor was cooled to 5° C., and then stirred at that temperature until crystallization is observed. 50 kg of ethanol was charged into the reactor and stirred at 5° C. for 30 minutes. The resulting slurry was filtered. An additional 19.7 kilograms of ethanol was charged into 50 gallon reactor and rinsed forward to the filter.

Solid material was transferred from the filter to drying trays. The solid material was dried under full vacuum at less than 65° C. for 12 hours using a nitrogen bleed on the dryer.

The product yield for this batch was 59%.

The analysis of sodium nitrite provided herein from the purification procedure is summarized in Table 1.

TABLE 1

| Analysis | Testing Result |
| --- | --- |
| USP Assay | 99.2% |
| Ion Chromatography | 99.8% |
| Sodium | Complies[a] |
| Nitrite | Complies[a] |
| pH of 10% solution at 25° C. | 7.9 |
| Loss on Drying | <0.01% |
| Heavy Metals | NMT 10 ppm |
| Sodium Nitrate | <0.05% |
| Sodium Carbonate | <0.01% |
| Insoluble Matter | 0.001% |
| Chloride | <0.005% |
| Sulfate | <0.01% |
| Iron | <0.001% |
| Calcium | <0.01% |
| Potassium | <0.001% |
| Ethanol | <0.1% (1000 ppm) |
| Total non-volatile organic carbon or equivalent | <5.6 ppm |
| Mercury | <0.05 ppm |
| Aluminum | <2 ppm |
| Arsenic | <1 ppm |
| Residual anti-caking agent | <10 ppm |
| Selenium ICP-OES or equivalent | <0.001% |
| Bacterial Endotoxins | <0.018 EU/mg |

[a]The identification of sodium and nitrite were determined using the identification tests, Method 191, as described in USP XXXII (2009).

During the drying, the sodium nitrite was tested at various intervals for its loss-on-drying and water content. Once the material reached suitable specifications for both loss on drying and water consent, the drying was stopped.

Example 2

Method of Determining the Total Non-volatile Organic Carbon in Sodium Nitrite Total non-volatile organic carbon was determined using an InnovOx laboratory TOC Analyzer (GE Analytical Instruments, Inc., Boulder, Colo.). Water used for standard, reagent, and sample preparation had total organic carbon (TOC) of no greater than 0.10 ppm. Phosphoric acid was ACS reagent grade. Sodium persulfate was obtained from General Electric. Sucrose USP was used as a reference standard. Compressed nitrogen has no greater than 1 ppm $CO_2$ and no greater than 1 ppm total hydrocarbon (THC).

Phosphoric acid (6 N) used as acidification solution was prepared by adding approximately 100 mL of water to a 250 mL volumetric flask, followed by the slow addition of 100 mL of phosphoric acid and adding additional water to make the final volume of 250 mL.

Sodium persulfate solution (30%) used as an oxidizer was prepared by adding 150 0.1 g of sodium persulfate to a 500 mL volumetric flask, and adding additional water to make the final volume of 500 mL, after the sodium persulfate was dissolved. The solution was allowed to sit for 3 days prior to use, and used within 14 days of the preparation.

The sucrose stock standard (250 ppm carbon based on 0.50 mg carbon/1.2 mg sucrose) was prepared by dissolving 9 mg of sucrose in 15 mL of water. TOC standard (10 ppm) was prepared by adding 4 mL of the sucrose stock standard to a 100 mL volumetric flask, followed by the addition of water to bring the volume to 100 mL at room temperature. TOC standard (2 ppm) was prepare by adding 10 mL of the 10 ppm TOC standard to a 50 mL volumetric flask, followed by the addition of water to bring the volume to 50 mL at room temperature. TOC standard (0.5 ppm) was prepare by adding 5 mL of the 10 ppm TOC standard to a 100 mL volumetric flask, followed by the addition of water to bring the volume to 100 mL at room temperature.

The sodium nitrite sample solution was prepared by adding 5.0 g of sample into a 100 mL volumetric flask, followed by the addition of water to bring the volume to 100 mL at room temperature.

The InnovOx instrument was calibrated with water, and the 0.5 ppm, 2 ppm, and 10 ppm TOC standards, using the following instrument parameters as shown in Table 2.

TABLE 2

| | |
|---|---|
| Protocol Name | Sodium Nitrite Cal |
| Number Points | 4 |
| Range | 0-1000 ppm |
| Acid | 6.0% |
| Oxidizer | 45.0% |
| Sparge | 4.0 min |
| Blank Correction | Off |
| Auto Dilution | Off |
| Cal Type | Pt—Pt |
| Replicates | 7 |
| Rejects | 2 |

The calibration curve requirements were that i) the correlation coefficient (r) of the average of the replicates must be no less than 0.99; ii) the RSD for the 2 and 10 ppm TOC standards must be no greater than 10%; iii) the limit of quantitation (LOQ) must be no greater than 3 ppm, which was calculated as follows:

$$LOQ=(10)(A)(B)/(C-D)$$

and iv) the limit of detection (LOD) must be no greater than 1 ppm, which was calculated as follows:

$$LOD=(3)(A)(B)/(C-D)$$

where:

A was the concentration of carbon in the 0.5 ppm TOC standard;

B was the standard deviation of the TOC concentration determined in the blank preparation;

C was the average TOC concentration determined in the 0.5 ppm TOC standard; and

D is the average TOC concentration determined in the blank preparation.

Samples were analyzed using the following instrument parameters as shown in Table 3.

TABLE 3

| | |
|---|---|
| Number Points | 4 |
| Range | 0-1000 ppm |
| Acid | 6.0% |
| Oxidizer | 45.0% |
| Sparge | 4.0 min |
| Flush | Dilution |
| Blank Correction | Off |
| Calibration | Sodium Nitrite Cal |
| Replicates | 6 |
| Rejects | 2 |

The 2 ppm TOC standard was run before and after each sample analysis.

The system suitability requirements were that i) the RSD for the 2 ppm TOC standard must be no greater than 10%; ii) the percentage of theoretical response (% T) for the 2 ppm TOC standard determinations must be no less than 90% and no greater than 110%; which was calculated as follows:

$$\% T=100 \times A/B;$$

where:

A was the result determined by the analyzer (ppm); and

B was the 2 ppm standard TOC concentration (ppm);

iii) for any sample that had a sample response at or above the LOQ, the RSD must be no greater than 15%; iv) the total organic carbon (TOC) equaled to A×20, where A was the result determined by the analyzer (ppm); if A is less than the LOD, the result was calculated using the LOD in the place of A, which sets the upper limit for the TOC, if A is less than the LOQ, but more than the LOD, the LOQ value sets the upper limit for the TOC.

Example 3

Determination of Nitrite and Nitrate Impurity in Sodium Nitrite

Standards and samples were prepared in purified water and analyzed by ion chromatography (IC) using an ion-exchange column (Dionex Ionpac AS12A) and suppressed conductivity detection. The separation was achieved by isocratic elution with aqueous mobile phase containing 2.7 mM sodium carbonate and 0.3 mM sodium bicarbonate. The performance parameters of system suitability, specificity, linearity and range, LOD/LOQ, accuracy, recovery, precision, intermediate precision, specificity, robustness, and analytical solution stability were evaluated. The LOD's were estimated to be 0.01 μg/mL for sodium nitrite and 0.04 μg/mL for sodium nitrate. The LOQ's were estimated to be 0.08 μg/mL for both compounds.

The linearity for sodium nitrite was evaluated using a series of standards at 60, 90, 120, 150, and 180 µg/mL. Each solution was injected in duplicate. The method was shown to be linear from 60 to 180 µg/mL of sodium nitrite with a correction coefficient (R) of 0.9999.

The linearity for sodium nitrite was evaluated using a series of standards ranging from 0.04 to 6.0 µg/mL. Each solution was injected in duplicate. The method was shown to be linear from 0.152 to 6.067 µg/mL of sodium nitrate with a correction coefficient (R) of 0.9997.

Example 4

Detection of Nitrogen Oxide Impurities in Sodium Nitrite

The concentration of total nitrogen oxides ($NO_xS$) in a sodium nitrite-containing solution was quantitated using nitrogen oxide ($NO_x$) electrode (Orion Model 94-46) by measuring electrode response (mV) and expressed in terms of µg/mL or ppm of nitrogen. The limit of detection for total nitrogen oxide impurities was determined to be about 1 ppm. Prior to the determination of total nitrogen oxide impurities, the pH meter was calibrated using the pH 4.0 and 7.0 buffers. The linearity of response of the $NO_x$ electrode was also determined using acidified 0.1 M KCl solution and various amounts of 1000 ppm $NO_x$ standard, which was prepared by dissolving 492±10 mg of sodium nitrite in water to a final 100 mL. Under pH<1.8, the nitrite at the concentration of 4.92 mg/mL is converted to equivalent amount of nitrogen oxides, and the corresponding concentration is 1000 mg/µL of nitrogen. The acidified 0.1 M KCl solution was prepared by mixing 15 mL 1 N HCl with 0.1 M KCl to a final volume of 500 mL. During the measurement, the solution was maintained at 20 to 25° C. and the pH of the sample sodium solution was no less than 6.7. The method was shown to be specific to $NO_x$ in the presence of nitrate and nitrite.

Example 5

Quantitation of Alkyl Naphthalene Sulfonates in Sodium Nitrite

A method was developed for quantitating alkyl naphthalene sulfonate (ANS) in a sodium nitrite-containing solution (e.g., 50 mg/mL). The method was used to determine ANS in the range of about 1 to about 200 ppm with a limit of detection of 0.3 ppm. Applied mass spectrometer and liquid chromatography were used for the quantitation of ANS in a sodium nitrite-containing sample.

Various standards of ANS in water ranging from 1 ng/mL to 10 mg/mL were prepared to determine the optimum detection mode and to optimize the detector parameters. Then spiked standards of ANS ranging from 1 ppm to 500 ppm in a solution of sodium nitrite (50 mg/mL) were prepared to test the range and linearity of the method.

The performance parameters of specificity, linearity and range, LOD/LOQ, accuracy, precision, and reproducibility were evaluated. The method, in conjunction with a quadratic regression, was shown to produce valid quantitative data within the range of 1 to 200 ppm with a correction coefficient (R) of 0.998.

Example 6

Preparation of Pharmaceutical Grade Sodium Thiosulfate Pentahydrate

Under nitrogen, 381.0 grams of sulfur and deionized water (3 L) were charged to an inerted 12 L four-necked flask with a torian, thermowell, reflux condenser, an overhead stirrer, and an Orion pH probe with pH meter. The slurry was stirred and 1000.1 grams of sodium sulfite and deionized water (2 L) were charged to the flask. The starting temperature was 20.9° C. and pH=10.2. The slurry was heated to 97° C. for 4 hours (pH at four hours=7.5). Heat was removed and the reaction was allowed to cool to room temperature overnight with stirring. The slurry was filtered with a 1.6 micron glass microfiber filter to give a clear yellow solution. The solution was then concentrated on a rotovac with a basin temperature of 60° C.+/−5° C. under a vacuum of 700-730 mm Hg. After 3 hours and 45 minutes, the solution had a specific gravity of 1.405 and the solution had a mass of 2,821 grams. The solution was transferred under nitrogen to a 5 liter, four-necked flask equipped with a torian, thermowell, and an overhead stirrer. The solution was cooled to 25° C. and a sample crystal of sodium thiosulfate pentahydrate was introduced into the solution. The solution was then cooled to 0+/−5° C. and stirred for 45 minutes. Precipitation began to occur as the solution reached 23.7° C. A white crystalline solid was filtered out using a fritted funnel. The mother liquor was used to rinse solids out of the reaction flask. The solid was transferred to drying dishes and placed overnight in a vacuum oven with a temperature of 20° C. During the drying, the sodium thiosulfate pentahydrate was tested at various intervals for its water content. Once the material reached suitable specifications for water content (i.e., about 32 to about 37% by weight) the drying was stopped. The dried solid had a final mass of 1016.2 grams (52% yield).

The examples set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed is:

1. An oral dosage form comprising sodium nitrite and one or more pharmaceutically acceptable carriers or excipients, wherein the sodium nitrite contains no greater than 0.02% by weight of sodium carbonate, contains no greater than 10 ppm of an anti-caking agent, has a loss on drying of no greater than 0.25% by weight, wherein the water content is no greater than 0.5% by weight, wherein the heavy metal content is no greater than 10 ppm, contains no greater than 0.4% by weight of sodium nitrate, contains no greater than 0.005% by weight of insoluble matter, contains no greater than 0.005% by weight of chloride, contains no greater than 0.01% by weight of sulfate, contains no greater than 0.001% by weight of iron, contains no greater than 0.01% by weight of calcium, contains no greater than 0.005% by weight of potassium, contains no greater than 0.05 ppm of mercury, contains no greater than 2 ppm of aluminum, contains no greater than 3 ppm of arsenic, contains no greater than 0.003% by weight of selenium, contains no greater than 5000 ppm of ethanol, contains no greater than 3000 ppm methanol, wherein the total non-volatile organic carbon content is no greater than 10 ppm, and contains no greater than 0.25 EU/mg of bacterial endotoxins;

wherein the sodium nitrite contains no less than 98% by weight of sodium nitrite;

wherein the sodium nitrite contains no less than 99.8% by weight of sodium nitrite as measured by Ion Chromatography analysis;

wherein a 10% aqueous solution of the sodium nitrite at 25° C. has a pH value between 8 and 9; and wherein the sodium nitrite has total aerobic count of microbial load of no greater than 100 CFU/g and has total yeast and mold count of no greater than 20 CFU/g.

2. The oral dosage form of claim 1, wherein the oral dosage form is a tablet, capsule, pill, troche, lozenge, pastille, cachet, pellet, medicated chewing gum, granule, bulk powder, effervescent or non-effervescent powder or granule, solution, emulsion, suspension, wafer, sprinkle, elixir, or syrup.

3. The oral dosage form of claim 1, wherein the oral dosage form is a tablet.

4. The oral dosage form of claim 1, wherein the oral dosage form is an enteric-coated tablet.

5. The oral dosage form of claim 1, wherein the oral dosage form is a tablet coated with a fatty acid, fat, salicylate, wax, shellac, ammoniated shellac or cellulose acetate phthalate.

6. The oral dosage form of claim 1, wherein the oral dosage form is a hard capsule.

7. The oral dosage form of claim 6, wherein the hard capsule comprises gelatin, methylcellulose, starch or calcium alginate.

8. The oral dosage form of claim 1, wherein the oral dosage form is a modified release dosage form comprising an erodible matrix device.

9. The oral dosage form of claim 8, wherein the erodible matrix device comprises a water-swellable, erodible or soluble polymer.

10. The oral dosage form of claim 8, wherein the erodible matrix device comprises hydroxypropyl methyl cellulose.

* * * * *